(12) United States Patent
Schlifke-Poschalko et al.

(10) Patent No.: US 8,883,829 B2
(45) Date of Patent: Nov. 11, 2014

(54) 2-PHENYL-1,2,3-BENZOTRIAZOLES FOR UV RADIATION ABSORBANCE

(75) Inventors: Alexander Schlifke-Poschalko, Basel (CH); Christine Mendrok-Edinger, Rheinfelden-Minseln (DE); Horst Westenfelder, Neustadt a.d.W. (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/521,576

(22) PCT Filed: Jan. 13, 2011

(86) PCT No.: PCT/EP2011/050392
§ 371 (c)(1),
(2), (4) Date: Oct. 15, 2012

(87) PCT Pub. No.: WO2011/086124
PCT Pub. Date: Jul. 21, 2011

(65) Prior Publication Data
US 2013/0142737 A1    Jun. 6, 2013

(30) Foreign Application Priority Data

Jan. 15, 2010 (EP) .................................... 10150832

(51) Int. Cl.
| | | |
|---|---|---|
| A61K 31/4192 | (2006.01) |
| C07D 249/20 | (2006.01) |
| A61Q 17/04 | (2006.01) |
| A61K 8/49 | (2006.01) |
| A61K 8/35 | (2006.01) |
| A61K 8/40 | (2006.01) |

(52) U.S. Cl.
CPC ................ *A61K 8/496* (2013.01); *A61Q 17/04* (2013.01); *A61K 8/35* (2013.01); *C07D 249/20* (2013.01); *A61K 8/40* (2013.01)
USPC .......................................... 514/359; 548/257

(58) Field of Classification Search
USPC .......................................... 514/359; 548/257
See application file for complete search history.

(56) References Cited

U.S. PATENT DOCUMENTS

2001/0007886 A1    7/2001 Ravichandran et al.
2010/0113641 A1*   5/2010 Laredo ........................... 523/107

FOREIGN PATENT DOCUMENTS

| CN | 1727338 | 2/2006 |
| JP | 8208628 | 8/1996 |
| WO | WO 2010/053917 | 5/2010 |

OTHER PUBLICATIONS

International Search Report for PCT/EP2011/050392 mailed Feb. 15, 2011.
Written Opinion of the International Searching Authority.

* cited by examiner

*Primary Examiner* — Rebecca Anderson
*Assistant Examiner* — Karen Cheng
(74) *Attorney, Agent, or Firm* — Nixon & Vanderhye P.C.

(57) ABSTRACT

The present invention relates to novel benzotriazoles and to novel topical compositions comprising these benzotriazoles. Furthermore, the invention relates to the use of the novel benzotriazoles as photostabilizer and solubilizer for dibenzoylmethane derivatives such as Butyl Methoxydibenzoylmethane. In one aspect the invention relates to novel benzotriazoles of formula (Ia) wherein $R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl; $R^3$ is hydrogen; $C_{1-5}$alkyl; $C_{1-5}$alkoxy or halogen, preferably hydrogen or Cl; $R^4$ is hydrogen or $C_{1-5}$alkyl; $R^5$ is $C_{1-30}$alkyl or $C_{5-10}$cycloalkyl.

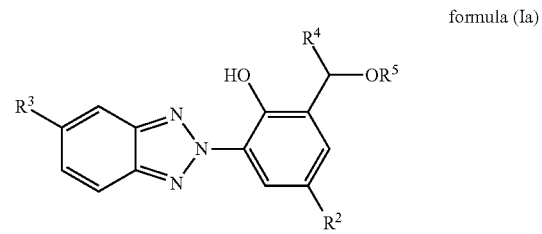

formula (Ia)

16 Claims, No Drawings

2-PHENYL-1,2,3-BENZOTRIAZOLES FOR UV RADIATION ABSORBANCE

This application is the U.S. national phase of International Application No. PCT/EP2011/050392 filed 13 Jan. 2011 which designated the U.S. and claims priority to EP 10150832.3 filed 15 Jan. 2010.

The present invention relates to novel benzotriazoles and to novel topical compositions comprising these benzotriazoles. Furthermore, the invention relates to the use of the novel benzotriazoles as photostabilizer and solubiliser for dibenzoylmethane derivatives such as Butyl Methoxydibenzoylmethane.

Sun care products have evolved considerably over the years. Earlier formulations were intended to protect the user from UV-B radiation (UVB) as was once thought that UV-B rays were the most important contributors to wrinkling, skin disease, and skin cancer. However, more recent studies have shown that UV-A radiation (UVA) is equally or even more important in the development of solar damage and skin diseases, such as lupus erythematosus and melanoma and non-melanoma skin cancers. Thus, today's focus is toward eliminating as much of UVA (320-400 nm) and/or UVB (280-320 nm) light as possible. This is reflected by novel regulations e.g. the EU recommendation 2006 which require the UVA protection to be at least one third of the UVB protection provided by the sun-care product or the FDA monograph proposal 2007 which introduces a star rating for UVA protection.

Due to the increasing demand for high SPF sun care products with a UVA protection complying with the above mentioned regulations, more UV-filter substances at elevated levels have to be incorporated into the sun care products;

In order to achieve the UVA protection required by the novel regulations today's sun-care products often contain Butyl Methoxydibenzoylmethane (BMDBM), the only globally approved UVA screening agent.

BMDBM, however, exhibits only a limited solubility in the conventional cosmetic oils used for the solubilisation of solid UV-filter substances in order to enable their incorporation into cosmetic preparations (such as e.g. the cosmetic oils $C_{12-15}$ alkyl benzoate or diisopropyl sebaceate), which is typically less than 20%. As a consequence sun-care products containing high amounts BMDBM require high amounts of such cosmetic oils in order to solubilize BMDBM and avoid a re-crystallization in the product, which in turn, however, often results in an unpleasant oily gritty and/or tacky skin feel of the final products and a reduction in UV protection performance.

Furthermore, BMDBM is photoinstable i.e. is degraded relatively quickly under the action of sunlight and, as a result, lose its protective action.

Thus, there is an ongoing need for compounds which are able to efficiently stabilize BMDBM and furthermore act as solubilizer for BMDBM in order to reduce the total amount of cosmetic oils used in sun care products. Furthermore, such compounds should be well soluble itself in such cosmetic oils such as in particular in Myritol 318 [INCI Capric/Caprylic Triglyceride] or Finsolv TN [INCI C12-15 Alkylbenzoate] or even be liquid and furthermore be accessible via a simple, economically attractive and environmentally benign method in order to be competitive in the market.

Surprisingly, it has been found that specific novel benzotriazoles fulfill the above mentioned requirements as they are accessible in good yields by means of simple industrial processes. Furthermore, the novel benzotriazoles efficiently stabilize BMDBM, are either liquid or well soluble in cosmetic oils such as in particular in Myritol 318 [INCI Capric/Caprylic Triglyceride] or Finsolv TN [INCI C12-15 Alkylbenzoate] and act as solubilizer for BMDBM which allows a reduction of the total amount of cosmetic oils.

Thus, in one aspect the invention relates to novel benzotriazoles of formula (I)

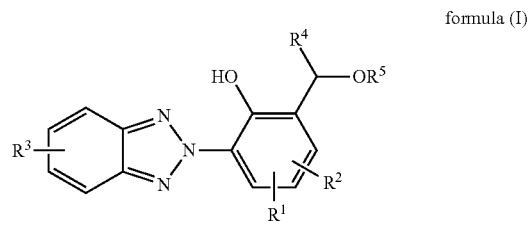

formula (I)

wherein
$R^1$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^3$ is hydrogen; $C_{1-5}$alkyl; $C_{1-5}$alkoxy or halogen, preferably hydrogen, Cl or hydroxy;
$R^4$ is hydrogen or $C_{1-5}$alkyl;
$R^5$ is $C_{1-30}$alkyl or $C_{5-10}$cycloalkyl.

In another aspect the invention relates to novel benzotriazoles of formula (Ia)

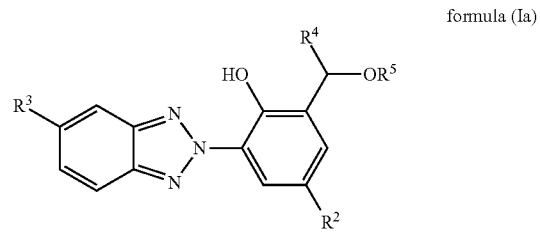

formula (Ia)

wherein
$R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^3$ is hydrogen; $C_{1-5}$alkyl; $C_{1-5}$alkoxy or halogen, preferably hydrogen or Cl, most preferably hydrogen;
$R^4$ is hydrogen or $C_{1-5}$alkyl; and
$R^5$ is $C_{1-30}$alkyl or $C_{5-10}$cycloalkyl.

In a particular embodiment the invention relates to compounds according to formula (II)

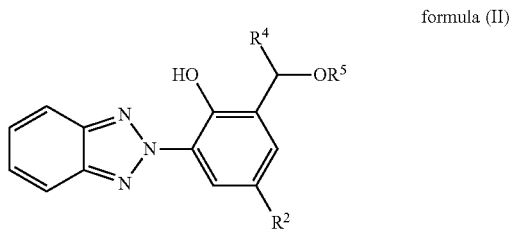

formula (II)

wherein
$R^2$ is hydrogen or $C_{1-12}$alkyl, preferably $C_{1-4}$alkyl, most preferably methyl;
$R^4$ is hydrogen or $C_{1-2}$alkyl; preferably hydrogen and $R^5$ is $C_{1-12}$alkyl or $C_{5-7}$cycloalkyl, preferably $C_{5-10}$alkyl or $C_6$cycloalkyl such as most preferably $C_{6-10}$alkyl or $C_6$cycloalkyl.

In another particular embodiment the invention relates to compounds according to formula (II), wherein
$R^2$ is methyl;
$R^4$ is hydrogen and
$R^5$ is $C_{5-10}$alkyl or $C_6$cycloalkyl such as $C_{6-10}$alkyl or $C_6$cycloalkyl such as in particular 2,5,5-trimethylhexyl, 3,5,5-trimethylhexyl, isoamyl, 2-ethylhexyl or 3,3,5-trimethylcyclohexyl.

$C_{1-30}$alkyl (encompassing $C_{1-2}$alkyl, $C_{1-5}$alkyl, $C_{5-10}$alkyl, $C_{6-10}$alkyl, $C_{1-12}$alkyl) denotes to straight-chain or branched alkyl radicals like methyl, ethyl, n-propyl, isopropyl, n-butyl, sec.butyl, tert.butyl, amyl, isoamyl or tert.amyl, hexyl, 2-ethylhexyl, heptyl, octyl, isooctyl, nonyl, decyl, undecyl, dodecyl, tetradecyl, pentadecyl, hexadecyl, heptadecyl, octadecyl or eicosyl without being limited thereto. Particularly advantageous are branched alkyl radicals such as particularly branched $C_{5-12}$alkyl radicals, more particularly branched $C_{5-10}$alkyl radicals such as branched $C_{6-10}$alkyl radicals such as e.g. 2,5,5-trimethylhexyl, 3,5,5-trimethylhexyl, isoamyl or 2-ethylhexyl as the corresponding benzotriazoles exhibit a particularly good solubility in the cosmetic oils Myritol 318 [INCI: Capric/Caprylic Triglyceride] respectively Finsolv TN [INCI: $C_{12-15}$ Alkylbenzoate].

Thus, in a specific embodiment the invention relates to compounds according to formula (Ia) such as in particular to compounds according to formula (II) wherein $R^5$ is a branched alkyl radical such as a branched $C_{5-10}$alkyl radical such as e.g. 2,5,5-trimethylhexyl, 3,5,5-trimethylhexyl, isoamyl or 2-ethylhexyl. In a even more specific embodiment the invention relates to compounds of formula (II) wherein $R^2$ is methyl; $R^4$ is hydrogen and $R^5$ is a branched alkyl radical such as a branched $C_{5-10}$alkyl radical such as e.g. 2,5,5-trimethylhexyl, 3,5,5-trimethylhexyl, isoamyl or 2-ethylhexyl.

$C_{5-10}$cycloalkyl (encompassing $C_{5-7}$cycloalkyl and $C_6$cycloalkyl) denotes to unsubstituted or $C_{1-10}$alkyl, in particular $C_{1-5}$alkyl substituted cyclic, bicyclic or tricyclic hydrocarbon residues such as in particular cyclopentyl, cyclohexyl, cycloheptyl or decahydronaphtyl. Preferably, $C_{5-10}$cycloalkyl (encompassing $C_{5-7}$cycloalkyl and $C_6$cycloalkyl) denotes to unsubstituted or $C_{1-2}$alkyl substituted cyclopentyl, cyclohexyl or cycloheptyl such as in particular to unsubstituted or methyl substituted cyclohexyl such as most in particular cyclohexyl or 3,3,5-trimethyl-cyclohexyl. Particularly preferred are methyl substituted cyclohexyl radicals such as particularly 3,3,5-trimethylcyclohexyl. Thus, in another specific embodiment the invention relates to compounds according to formula (Ia) such as in particular to compounds according to formula (II) wherein $R^5$ is a methyl substituted cyclohexyl radical such as particularly 3,3,5-trimethylcyclohexyl. In a even more specific embodiment the invention relates to compounds of formula (II) wherein $R^2$ is methyl; $R^4$ is hydrogen and $R^5$ is a methyl substituted cyclohexyl such as particularly 3,3,5-trimethylcyclohexyl.

$C_{1-5}$alkoxy is for example methoxy, ethoxy, propoxy, butyloxy or pentyloxy.

$C_{6-10}$aryl is for example naphthyl or phenyl, preferably phenyl.

If the benzotriazole structure of formula (I), (Ia) or (II) exhibits one or more stereocenter the present invention encompasses the optically pure isomers or pure enantiomers as well as mixtures of different isomers, e.g. racemates, and/or mixtures of rotamers. If applicable, mixtures of different isomers, e.g. racemates, and/or mixtures of rotamers are preferred.

The benzotriazoles according to the present invention are accessible in high yields by a simple two step synthesis using readily available raw materials as depicted below by chloroalkylation of a benzotriazole of formula (III) with an appropriate aldehyde $R^4$CHO followed by conversion of the obtained chloroalkylated benzotriazole with the respective alcohol to the corresponding benzotriazoles according to the present invention:

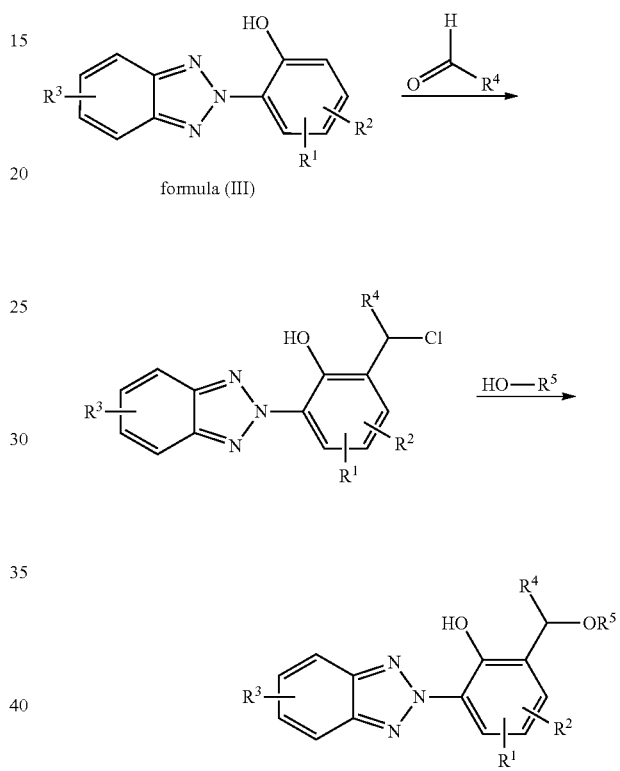

formula (III)

Thus, the invention also relates to a process for the preparation of benzotriazoles according to the invention comprising the steps of
a.) chloroalkylation of a benzotriazole of formula (III), such as of formula (IIIa) and in particular of formula (IV) with an aldehyde $R^4$CHO

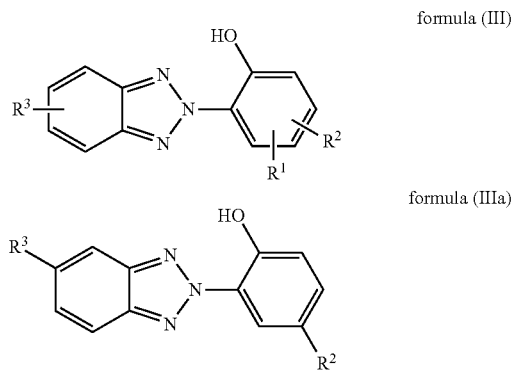

formula (III)

formula (IIIa)

-continued formula (IV)

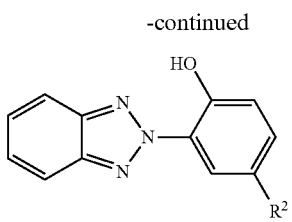

followed by
b.) ether formation by conversion of the chloroalkylated benzotriazole with an alcohol $R^5OH$ in the presence of a base
wherein
$R^1$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^3$ is hydrogen; $C_{1-5}$alkyl; $C_{1-5}$alkoxy or halogen, preferably hydrogen, Cl or hydroxy;
$R^4$ is hydrogen or $C_{1-5}$alkyl;
$R^5$ is $C_{1-30}$alkyl or $C_{5-10}$cycloalkyl.

Advantageously, a compound of formula (IIIa) wherein $R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl; $R^3$ is hydrogen; $C_{1-5}$alkyl; $C_{1-5}$alkoxy or halogen, preferably hydrogen or Cl; an aldehyde wherein $R^4$ is hydrogen or $C_{1-5}$alkyl; and an alcohol wherein $R^5$ is $C_{1-30}$alkyl or $C_{5-10}$cycloalkyl are used in the process according to the invention.

Preferably, a compound of formula (IV) wherein $R^2$ is hydrogen or $C_{1-12}$alkyl, preferably $C_{1-4}$alkyl most preferably methyl; an aldehyde wherein $R^4$ is hydrogen or $C_{1-2}$alkyl; and an alcohol wherein $R^5$ is $C_{1-12}$alkyl or $C_{5-7}$cycloalkyl, preferably $C_{5-10}$alkyl or $C_6$cycloalkyl such as particularly $C_{6-10}$alkyl or $C_6$cycloalkyl are used in the process according to the invention. Even more in particular a compound of formula (IV) wherein $R^2$ is methyl; an aldehyde wherein $R^4$ is hydrogen and an alcohol wherein $R^5$ is $C_{1-12}$alkyl or $C_{5-7}$cycloalkyl such as in particular $C_{5-10}$alkyl or $C_6$cycloalkyl and more in particular $C_{6-10}$alkyl or $C_6$cycloalkyl such as in particular 3,5,5-trimethylhexyl, 2,5,5-trimethylhexyl, 3,3,5-trimethylcyclohexyl, isoamyl or 2-ethylhexyl are used.

Suitable aldehydes $R^4CHO$ to be used in the process according to the invention encompass in particular formaldehyde and acetaldehyde and sources of formaldehyde such as paraformaldehyde or hexamethylenetetramine. Particularly preferred is the use of formaldehyde and sources of formaldehyde such as paraformaldehyde or hexamethylenetetramine.

Particular suitable benzotriazoles of formula (III) are 2-(2H-benzotriazol-2-yl)-4-methyl-phenol, 2-(2H-benzotriazol-2-yl)-4-(2-hydroxy-ethyl)phenol, 2-(2H-benzotriazol-2-yl)-4-(1,1,3,3-tetramethyl-butyl)-phenol, and 2-(2H-benzotriazol-2-yl)-4-tert-butyl-phenol.

Particular suitable alcohols $R^5OH$ in the process according to the present invention are methanol, ethanol, n-propanol, i-propanol, 1-butanol, 2-butanol, tert.-butanol, 2-ethyl-1-butanol, 2-methyl-1-butanol, 1-pentanol, 2-pentanol, 3-pentanol, 4-methyl-2-pentanol, 3-methyl-1-pentanol, 2-methyl-1-pentanol, 1-hexanol, 2-hexanol, 3-hexanol, 2-methyl-3-hexanol, 5-methyl-2-hexanol, 5-methyl-1-hexanol, 2,2-dimethyl-3-hexanol, 4-ethyl-3-hexanol, 3-methyl-1-hexanol, 2,5-dimethyl-3-hexanol, 1-heptanol, 2-heptanol, 3-heptanol, 5-methyl-3-heptanol, 2,4-dimethyl-3-heptanol, 6-methyl-2-heptanol, 4-methyl-3-heptanol, 2,6-dimethyl-4-heptanol, 2,6-dimethyl-2-heptanol, 1-octanol, 2-octanol, 3-octanol, 4-octanol, 2-butyl-1-octanol, 3,7-dimethyl-1-octanol, 1-nonanol, 2-nonanol, 3-nonanol, 4-nonanol, 5-nonanol, 2,6,8-trimethyl-4-nonanol, 1-decanol, 2-decanol, 4-decanol, 1-undecanol, 2-undecanol, 3-undecanol, 6-undecanol, 1-dodecanol, cyclohexanol, 4-ethylcyclohexanol, 4-methylcyclohexanol, 3-methylcyclohexanol, 2-methylcyclohexanol, 2,3-dimethylcyclohexanol, 4-butylcyclohexanol, 2-tert-butylcyclohexanol, 4-tert-butyl-cyclohexanol, 4-tert-amylcyclohexanol, cyclohexanemethanol, 2-cyclohexylethanol, 3-cyclohexyl-1-propanol, 4-methyl-1-cyclohexanemethanol, 2-cyclohexylcyclohexanol, 1-cyclohexyl-1-butanol, cyclooctanol, cyclopentanol, cycloheptanol, decahydro-2-naphthol, borneol, isoborneol, isopinocampheol, menthol, isomenthol, neomenthol, myrtanol, tetrahydrolavandulol, 2-norboranemethanol, 1-adamantanol, 2-adamantanol, isoamylalcohol such as in particular hexanol, isoamylalcohol, 2,5,5-trimethylhexan-1-ol, 2-ethylhexanol, 3,3,5-trimethylcyclohexanol or 3,5,5-trimethylhexan-1-ol as well as mixtures thereof. It is particularly advantageous to use branched alkyl alcohols in the processes according to the invention, such as branched $C_{5-12}$ alcohols, in particular branched $C_{5-10}$ alcohols or even branched $C_{6-10}$ alcohols such as e.g. isoamylalcohol, 2,5,5-trimethylhexan-1-ol, 2-ethylhexanol, or 3,5,5-trimethylhexan-1-ol as this leads to particularly well suitable benzotriazoles in the cosmetic oils selected from Myritol 318 [INCI Capric/Caprylic Triglyceride] and Finsolv TN [INCI C12-15 Alkylbenzoate]. Further advantageous is the use of methyl substituted cyclohexanols such as e.g. 3,3,5-trimethylcyclohexanol.

The chloroalkylation can be performed according to known methods for reacting aromatic compounds with hydrogen chloride and an appropriate aldehyde in the presence of a Lewis acid or a proton acid as a catalyst or mixtures thereof. The amount of aldehyde employed in the chloroalkylation reaction may be the stoichiometric amount, i.e., the amount which provides one $R^4$ group per benzotriazole. Preferably a slight excess is used in order to achieve full conversion and good yields. Particularly, zinc chloride is used as catalyst and the reaction is carried out in acetic acid. The reaction temperature may vary from about 70° C. to 130° C. Preferably, the reaction temperature ranges from about 70° C. to 100° C., even more preferably from about 65-85° C. The amount of hydrogen chloride used in the reaction is usually at least about one mol equivalent, based on the amount of the benzotriazole; and it is generally introduced by bubbling it through the reaction mixture or by pressurizing the reaction vessel with it.

The ether formation may be performed by nucleophilic substitution of the chloride with an alkoxide (Williamson ether synthesis). The alkoxides are usually prepared immediately prior to the reaction, or are generated in situ from the respective alcohol with a base such as e.g. a carbonate base, a phase transfer catalyst, potassium hydroxide, potassium tert.butylate, dipotassium hydrogenphosphate, sodium, sodium methoxide or sodium hydride such as in particular an alkali metal and/or alkaline earth metal carbonate or bicarbonate such as particularly sodium carbonate, potassium carbonate or lithium carbonate, potassium tert.butylate, sodium hydride, sodium, sodium methylate or dipotassium hydrogenphosphate. A wide range of solvents can be used in the process according to the present invention such as in particular toluene, acetonitrile, N,N-dimethylformamide, tetrahydrofuran or dioxane. In another embodiment, the reaction is carried out in an excess of the corresponding alcohol $R^5$—OH itself. Preferably, the reaction according to the present invention is carried out in toluene, dioxane or tetrahydrofuran. Typically the reaction is conducted at 50-100° C. and is complete in 1-15 hours. Catalysis is not usually necessary however, if deemed appropriate; the rate of reaction can be further improved by the addition of a catalytic quantity of a soluble iodide. In extreme cases, silver salts may be added for example silver oxide.

Each reaction of the process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

The benzotriazoles according to the present invention are useful to act as solubiliser for solid, oil soluble UV-filter substances such as BMDBM, bis-ethylhexyloxyphenol methoxyphenyl triazine, benzophenone-3, drometrizole trisiloxane, ethylhexyl triazone, diethylhexyl butamido triazone, 4-methyl benzylidene camphor or 2-(4-Diethylamino-2-hydroxy-benzoyl)-benzoic acid hexylester, in particular BMDBM in cosmetic oils suitable as solvents for such solid, oil soluble UV-filter substances and suitable for the preparation of topical compositions such as in particular in $C_{12-15}$ alkyl benzoate, caprylic/capric triglyceride, dicaprylyl carbonate or diisopropyl sebacate. Furthermore, the benzotriazoles according to the present invention efficiently stabilize BMDBM from photo-degradation.

Furthermore, the benzotriazoles according to the invention are useful as UV filter substances, i.e. for protecting ultraviolet-sensitive organic materials, in particular the skin and hair of humans and animals from the harmful effects of UV radiation. The benzotriazoles according to the present invention are not only suitable for "immediate protection from acute sun damage" such as sun burn (sun erythema), but also protect against damages through sunlight-induced oxidative stress and/or immune suppression and/or their consequences, i.e. photo aging. Furthermore, the benzotriazoles according to the present invention are also suitable to protect natural or artificial hair color. The benzotriazoles according to the present invention also lead to a synergistic UV-light absorption if used in combination with at least one further UV-filter substance. Furthermore, the benzotriazoles according to the present invention are suitable to reduce the stickiness e.g. of sand on the skin as well as to enhance the water resistance.

The benzotriazoles according to the present invention are colorless or yellowish, liquid, crystalline or semi-liquid substances. Preferably, the benzotriazoles according to the present invention are liquid non-crystalline substances. They are distinguished by high photostability, good solubility in organic solvents, especially cosmetic solvents such as in particular in $C_{12-15}$ alkyl benzoate (e.g., FINSOLV TN [Finetex Inc.]), caprylic/capric triglyceride, dicaprylyl carbonate or diisopropyl sebacate, and a short and economical synthetic route.

Due to their properties and in particular their excellent solubility, the benzotriazoles according to the present invention can be easily incorporated into topical compositions such as sunscreens. Thus, the present invention also relates to compositions, preferably to topical compositions comprising a benzotriazole according to the present invention and a cosmetically or pharmaceutically acceptable carrier.

The amount of the benzotriazole in the compositions according to the invention is not critical. Preferably an amount of at least 0.01 wt.-% is used. More preferably an amount of 0.5 to 20 wt.-%, in particular 1 to 10 wt.-% such as e.g. from about 2 to 10 wt.-% based on the total weight of the composition is incorporated into the compositions.

In a particular embodiment, the compositions according to the invention further comprise an additional amount of an oil soluble, solid UV-filter substance. Suitable oil soluble, solid UV-filter substances are in particular butyl methoxydibenzoylmethane (BMDBM), bis-ethylhexyloxyphenol methoxyphenyl triazine (BEMT), benzophenone-3, drometrizole trisiloxane, ethylhexyl triazone, diethylhexyl butamido triazone, 4-methyl benzylidene camphor or 2-(4-Diethylamino-2-hydroxy-benzoyl)-benzoic acid hexylester as well as mixtures thereof.

In a particular embodiment, the topical composition according to the invention further comprises BMDBM as oil soluble, solid UV-filter substance in an amount of at least 0.01 wt.-%. Particularly, the topical composition comprises BMDBM in an amount of 0.5 to 5 wt.-%, most in particular in an amount of 2 to 5 wt.-% based on the total weight of the composition. It is further advantageous if the compositions further comprise an effective amount of octocrylene.

In a further particular embodiment, the topical composition according to the invention further comprises bis-ethylhexyloxyphenol methoxyphenyl triazine in an amount of at least 0.01 wt.-%. Particularly, the topical composition comprises bis-ethylhexyloxyphenol methoxyphenyl triazine in an amount of 0.5 to 5 wt.-%, most in particular in an amount of 1 to 3 wt.-% based on the total weight of the composition. It is further advantageous if the compositions further comprise an effective amount of octocrylene. Suitable amounts of octocrylene may range from 0.5 to 20 wt.-%, such as from 1 to 10 wt.-% with respect to the total weigh of the composition.

It is also particularly advantageous if the topical composition according to the present invention comprises as solid UV absorbers BMDBM and bis-ethylhexyloxyphenol methoxyphenyl triazine in the amounts given above. Particularly BMDBM is incorporated in an amount of 2 to 5 wt.-% and bis-ethylhexyloxyphenol methoxyphenyl triazine in an amount of 1 to 3 wt.-% based on the total weight of the composition. Suitable amounts of octocrylene may range from 0.5 to 20 wt.-%, such as from 1 to 10 wt.-% with respect to the total weigh of the composition.

In another particular embodiment, the invention relates to a topical composition according to the invention comprising a benzotriazole with the definitions and preferences as outlined above which further comprises octocrylene in an amount of at least 0.01 wt.-%. Particularly, octocrylene is present in an amount of 0.5 to 10 wt.-%, most in particular in an amount of 2 to 8 wt.-% based on the total weight of the composition. Furthermore, it is advantageous to use the benzotriazole according to the invention and octocrylene in a ratio (w/w) of about 1-2 to 3-1 such as about 2.5-1 to 2-1. It is further preferred to add BMDBM in an amount of at least 0.01 wt.-%, such as particularly 0.5 to 5 wt.-%, most in particular 2 to 5 wt.-% based on the total weight of the composition into a composition comprising a benzotriazole according to the invention and octocrylene Where convenient other conventional UV-filter substances may be added into the topical compositions of the invention. The combination of UV-filter substances may show a synergistic effect. These additional UV-filter substances are advantageously selected from among acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2',4,4'-tetrahydroxy-benzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as polysilicone-15 (PARSOL® SLX); drometrizole trisiloxane (Mexoryl® XL); imidazole derivatives such as e.g. 2-phenyl benzimidazole sulfonic acid and its salts (PARSOL® HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate (PARSOL® EHS, Neo Heliopan® OS), isooctyl salicylate or homomethyl salicylate (homosalate, PARSOL® HMS, Neo Heliopan® HMS) and the like; triazine derivatives such as ethylhexyl triazone (Uvinul® T-150), diethylhexyl butamido triazone ethylhexyl triazone (Uvinul® T-150), diethylhexyl butamido triazone (Uvasorb® HEB), 2,4,6-Tris-(biphenyl)1,3,5-triazine and the like, merocyanines as e.g. disclosed in DE10 2007 024 345 on page 4, paragraph 19 which are incorporated by reference herein, encapsulated UV-filters such as encapsulated ethylhexyl methoxycinnamate (Eusolex® UV-pearls) or microcapsules loaded with UV-filters as e.g. disclosed in EP 1471995 and the like; dibenzoylmethane derivatives such as 4-tert.-butyl-4'-methoxydibenzoylmethane (PARSOL® 1789) or isopropyldibenzoylmethane and the like; benzotriazole derivatives such as 2,2'-methylene-bis-(6-(2H-benzotriazole-2-yl)-4-(1,1,3,3,-tetramethylbutyl)-phenol (Tinosorb® M) and the like; bis-ethylhexyloxyphenol methoxyphenyl triazine (Tinosorb® S) and the like; phenylene-1,4-bis-benzimidazolsulfonic acids or salts such as 2,2-(1,4-phenylene)bis-(1H-benzimidazol-4,6-disulfonic acid) (Neo Heliopan® AP); amino substituted hydroxybenzophenones such as 2-(4-Diethylamino-2-hydroxy-benzoyl)-benzoic acid hexylester (Uvinul® A plus) or 1,1'-(1,4-piperazinediyl)bis[1-[2-[4-(diethylamino)-2-hydroxybenzoyl]phenyl]-methanone (CAS No 919803-06-8); Ionic UV-A filters as described in the International Patent Publication WO2005080341 A1; pigments such as microparticulated ZnO or TiO$_2$ and the like. The term "microparticulated" refers to a particle size from about 5 nm to about 200 nm, particularly from about 15 nm to about 100 nm. The pigments may also be coated by other metal oxides such as e.g. aluminum or zirconium oxides or by organic coatings such as e.g. polyols, methicone, aluminum stearate, alkyl silane. Such coatings are well known in the art. Furthermore, the pigments (ZnO, TiO$_2$) can be used in the form of commercially available oily or aqueous pre-dispersions. These pre-dispersions may further contain a dispersing aid and/or solubilisator.

Particularly preferred additional UV-filter substances to be used in combination with a benzotriazole according to the present invention are the commercially available and widely used UV-filter substances octocrylene (PARSOL® 340), 4-methyl benzylidene camphor (PARSOL® 5000), ethylhexyl methoxycinnamate (PARSOL® MCX), ethylhexyl triazone (Uvinul® T-150), diethylhexyl butamido triazone (Uvasorb® HEB), 2,2'-methylene-bis-(6-(2H-benzotriazole-2-yl)-4-(1,1,3,3,-tetramethylbutyl)-phenol (Tinosorb® M), bis-ethylhexyloxyphenol methoxyphenyl triazine (Tinosorb® S), 2,2-(1,4-phenylene)bis-(1H-benzimidazol-4,6-disulfonic acid (NeoHeliopan® AP), 2-(4-Diethylamino-2-hydroxy-benzoyl)-benzoic acid hexylester (Uvinul® A plus), 1,1-(1,4-piperazinediyl)bis[1-[2-[4-(diethylamino)-2-hydroxybenzoyl]phenyl]methanone (CAS No 919803-06-8), polysilicone-15 (PARSOL® SLX), 2-phenyl benzimidazole sulfonic acid (PARSOL® HS), ethylhexyl salicylate (PARSOL® EHS), homomethyl salicylate (PARSOL® HMS), Benzophenone-3 (Uvinul® M 40), Benzophenone-4 (Uvinul® MS 40), microfine zinc or titanium dioxide such as in particular PARSOL® TX as well as mixtures thereof. Thus, particularly preferred combinations of UV-filters are e.g. the combination of a benzotriazole according to the invention, octocrylene, BMDBM and 2-(4-Diethylamino-2-hydroxybenzoyl)-benzoic acid hexylester; a benzotriazole according to the invention, octocrylene, BMDBM, bis-ethylhexyloxyphenol methoxyphenyl triazine and 2,2'-methylene-bis-(6-(2H-benzotriazole-2-yl)-4-(1,1,3,3,-tetramethylbutyl)-phenol as well as the combination of a benzotriazole according to the invention with a pigment such as microparticulated ZnO or TiO$_2$ such as in particular PARSOL® TX.

The additional UV-filter substances are generally present in the compositions according to the invention in proportions ranging from 0.1 to 30 wt.-%, preferably ranging from 0.2 to 15 wt.-%, most preferably ranging from 0.5 to 10 wt.-% with respect to the total weigh of the composition.

As dibenzoylmethane derivatives in particular BMDBM have a limited photostability it may be desirable to further photostabilize these UV-filter substances in the topical compositions according to the invention. Thus, the invention also relates to topical compositions according to the invention which next to a dibenzoylmethane derivative such as in particular BMDBM also contain an effective amount of a further stabilizer. The term effective amount of a stabilizer refers to an amount suitable for the photostabilization of a dibenzoylmethane derivative. The amount may vary from stabilizer to stabilizer (e.g. based on the mode of action) and can easily been determined by a person skilled in the art with normal trials, or with the usual considerations regarding the formulation of cosmetic composition. Suitable amounts may range from 0.01 to 1 wt.-% as well as from 0.5 to 20 wt.-%, such as 1 to 10 wt.-% with respect to the total weigh of the composition.

Suitable stabilizers next to the benzotriazoles according to the present invention include octocrylene, diethylhexyl-2,6-naphthalate, polyester-8, diethylhexyl syringylidenemalonat, butyloctyl salicylate, polysilicone-15, tris(tetramethylhydroxypiperidinol)citrate, benzotriazolyl dodecyl p-cresol, benzophenone-3,4-methylbenzylidene camphor, Methoxycrylene (Solastay S1) and/or bis ethylhexyloxyphenol methoxyphenyl triazine. Particularly suitable as stabilizer is octocrylene.

Thus, in a further embodiment, the invention also relates to a topical composition comprising a benzotriazole according to the invention, BMDBM and octocrylene or Methoxycrylene, in particular octocrylene, preferably the benzotriazole is used in an amount of 0.5 to 20 wt.-%, BMDBM in an amount of 2 to 5 wt.-% and octocrylene in an amount of 2 to 10 wt.-%.

In another particular embodiment the topical compositions according to the present invention are free of p-methylbenzylidene camphor.

Preferably, the topical compositions according to the present invention furthermore contain one or more preservatives such as e.g. Methylparabene, Ethylparabene, Propylparabene or Butylparabene, Isobutylparabene, Benzoic Acid and its salts (e.g. Sodium Benzoate), Sorbic Acid and its salts (e.g. Potassium Sorbate, Dehydracetic Acid and its salts, Bronopol, Triclosan, Imidazolidinyl Urea, Phenoxyethanol, Benzyl Alcohol, Methylchloroisothiazolinone, Methylisothiazolinone, Chlorphenesin, Ethylhexylglycerin, Iodopropinylbutylcarbamate or Pentylene Glycol as well as mixtures thereof and without being limited thereto. A total content of about 0.01 to 2 wt.-%, such as in particular 0.05 to 1 wt.-% of preservatives with respect to the total weight of the composition is preferred.

The topical compositions according to the present invention may in particular contain further ingredients such as moisturizers; anti-oxidants; insect repellents; ingredients for skin lightening, tanning prevention and/or treatment of hyperpigmentation; tanning agents, ingredients for preventing or reducing wrinkles, lines, atrophy and/or inflammation; as well as topical anesthetics.

Particularly suitable moisturizers for the incorporation into the topical compositions according to the invention are glycerin, lactic acid and/or lactates, in particular sodium lactate, butylene glycol, propylene glycol, biosaccaride gum-1, glycine soja, ethylhexyloxyglycerin, pyrrolidoncarboxy acid, hydroxyethylurea and urea. It is further advantageous to use polymeric moisturizer such as water soluble or water gelifiable polysaccharides. In particular advantageous are e.g. hyaluronic acid, chitosan, Pentavitin and/or a polysaccharid rich in fucose [CAS No 178463-23-5, commercially available as Fucogel®1000 by SOLABIA S.A.]. The moisturizers can also be used as anti-ageing ingredients such as e.g. for the treatment of photo-aged skin.

The topical compositions according to the invention preferably contain at least one moisturizer in an amount (in total) of 0.1 to 20 wt.-%, preferably 0.5 to 10 wt.-% based on the total weight of the composition.

Particularly suited antioxidants for the topical compositions according to the invention encompass vitamin E and its derivatives such as particularly tocopheryl acetate. Tocopheryl acetate may be present in the topical compositions in an amount from about 0.05 wt.-% to 25 wt.-%, in particular 0.05 wt.-% to 5 wt.-%. Another vitamin E derivative of interest is tocopheryl linoleate. Tocopheryl linoleate may be present in the topical composition in an amount from about 0.05 wt.-% to 25 wt.-% in particular 0.05 wt.-% to 5 wt.-%.

Another suitable antioxidant is vitamin A and/or its derivatives. In particular retinoid derivatives such as retinyl palmitate or retinyl propionate is used in the topical compositions according to the invention in an amount of 0.01 to 5 wt.-%, in particular 0.01 to 0.3 wt.-%. The vitamin A and/or its derivatives can also be used in an encapsulated form.

Another suitable antioxidant is Vitamin C (ascorbic acid) and/or its derivatives. In particular ascorbyl phosphate such as Stay C (sodium ascorbyl monophosphate) Mg ascorbylphosphate and or Ascorbylglucoside is used in the topical compositions according to the invention in an amount of 0.1 to 5 wt.-% in particular 0.1 to 2 wt.-%.

Suitable insect repellents include N,N-Diethyl-3-methylbenzamid (Meta-delphene, "DEET"), Dimethylphtalat (Palatinol M, DMP), 1-Piperidincarbonsaure-2-(2-hydroxyethyl)-1-methylpropylester as well as particularly 3-(N-n-Butyl-N-acetyl-amino)-propionic acid (available as Insect Repellent® 3535 at Merck) as well as mixtures thereof.

Suitable skin lightening (depigmentation) agents to be used in the topical compositions according to the invention encompass alpha-arbutin, resveratrol, hydroquinone, azelaic acid, kojic acid as well as ascorbyl phosphates such as Magnesium-L-ascorbyl-2-phosphate (MAP), sodium ascorbyl monophosphate or ascorbylglucoside Suitable tanning agents are dihydroxyacetone, erythrulose and/or melanine derivates in an amount of 1 to 10 wt.-% based on the total weight of the composition according to the invention.

Further examples of cosmetically active ingredients suitable to be used in the topical composition according to the invention comprise peptides (e.g., Matrixyl™ [pentapeptide derivative]), oligopeptides, wax-based synthetic peptides (e.g., octyl palmitate and tribehenin and sorbitan isostearate and palmitoyl-oligopeptide), glycerol, alpha-glycosylrutin, natural or synthetic flavanoids or isoflavanoids, creatine, creatinine, guanidine (e.g. amino guanidine); vitamins and derivatives thereof such as vitamin C (ascorbic acid), vitamin A (e.g., retinoid derivatives such as retinyl palmitate or retinyl propionate), vitamin E (e.g., tocopherol acetate), vitamin $B_3$ (e.g. niacinamide) and vitamin $B_5$ (e.g. panthenol), vitamin $B_6$ and vitamin $B_{12}$, biotin, folic acid; anti-acne actives or medicaments (e.g. resorcinol, salicylic acid, and the like); antioxidants (e.g. phytosterols, lipoic acid); flavonoids (e.g. isoflavones, phytoestrogens); skin soothing and healing agents such as aloe vera extract, allantoin and the like; agents suitable for aesthetic purposes such as essential oils, fragrances, skin sensates, opacifiers, aromatic compounds (e.g., clove oil, menthol, camphor, eucalyptus oil, and eugenol), desquamatory actives, hydroxy acids such as AHA acids, poly unsaturated fatty acids, radical scavengers, farnesol, antifungal actives in particular bisabolol, alkyldiols such as 1,2-pentanediol, hexanediol or 1,2-octanediol, phytol, polyols such as phytanetriol, ceramides and pseudoceramides, amino acids, protein hydrolysates, polyunsaturated fatty acids, plant extracts like kinetin, DNA or RNA and their fragmentation products, carbohydrates, conjugated fatty acids, carnitin, carnosine, biochinonen, phytofluen, phytoen, and their corresponding derivatives and co-enzyme Q10 (ubiquinone) without being limited thereto.

The additional cosmetically active ingredient is typically included in an amount of at least 0.001 wt.-% based on the total weight of the topical composition. Generally, an amount of about 0.001 wt.-% to about 30 wt.-%, preferably from about 0.001 wt.-% to about 10 wt.-% of an additional cosmetically active agent is used.

Particularly preferred examples of ingredients to be used in the compositions according to the invention are vitamin C (ascorbic acid) and/or its derivatives (e.g. ascorbyl phosphate such as Stay C (sodium ascorbyl monophosphate) from DSM Nutritional Products Ltd.), vitamin A and/or its derivatives (e.g., retinoid derivatives such as retinyl palmitate or retinyl propionate), vitamin E and/or its derivatives (e.g., tocopherol acetate), vitamin $B_6$, vitamin $B_{12}$, biotin and/or co-enzyme Q10.

The topical cosmetic compositions of the invention can also contain usual cosmetic or pharmaceutical adjuvants and additives, such as preservatives, film forming agents, antioxidants, fatty substances/oils and/or waxes, water, organic solvents, silicones, thickeners, softeners, emulsifiers, antifoaming agents, aesthetic components such as fragrances, surfactants, fillers, sequestering agents, anionic, cationic, nonionic or amphoteric polymers or mixtures thereof, propellants, acidifying or basifying agents, complexing agents, dyes, colorings/colorants, abrasives, absorbents, essential oils, skin sensates, astringents, perfumes or any other ingredients usually formulated into cosmetic compositions such as alcohols, polyols or electrolytes. Such cosmetic ingredients commonly used in the skin care industry, which are suitable for use in the compositions of the present invention are e.g. described in the CTFA Cosmetic Ingredient Handbook, Second Edition (1992) without being limited thereto.

The necessary amounts of the cosmetic and pharmaceutical adjuvants and additives can—based on the desired product form—easily be chosen by a skilled person in this field and will be illustrated in the examples, without being limited hereto.

The usual cosmetic adjuvants and additives such as e.g. emulsifiers, thickeners, surface active ingredients and film formers can show synergistic effects which can be determined by the expert in the field with normal trials, or with the usual considerations regarding the formulation of cosmetic composition.

The fatty substances can be an oil or a wax, or mixtures thereof. By the term "oil" is intended a compound which is liquid at ambient temperature. By the term "wax" is intended a compound which is solid or substantially solid at ambient temperature and for which the melting point is generally greater than 35° C.

Exemplary oils are mineral oils (liquid paraffin); vegetable oils (sweet almond, macadamia, blackcurrant seed or jojoba oil); synthetic oils, such as perhydrosqualene, fatty alcohols, acids or esters (such as the $C_{12-15}$ alkyl benzoate marketed under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; polyalkylenes and their mixtures.

Preferably the oils used in the compositions according to the invention are selected from the list of polar oils such as the lecitines and fatty acid triglycerides, namely triglycerinester of saturated or unsaturated, branched or linear alkanoic acids with a chain length of 8 to 24, particularly 12 to 18 C-atoms. The fatty acid triglycerides may preferably be selected from the group of synthetic, semi synthetic and natural oils such as e.g. cocoglyceride, olive oil, sunflower oil, soy bean oil, peanut oil, palm oil, sweet almond oil macadamia oil, coconut oil etc.

Further particularly suitable are natural waxes such as bees wax, shea butter, and/or lanolin. Further particularly suitable polar oils according to the present invention may be selected from the group of esters of saturated or unsaturated, branched or linear alkanoic acids with a chain length of 3 to 30 C-atoms and saturated or unsaturated, branched or linear alcohols with a chain length of 3 to 30C-atoms as well as from the group of esters from aromatic carbonic acids and saturated or unsaturated, branched or linear alcohols with a chain length of 3 to 30C-atoms. Such ester oils are particularly selected from the group of phenylethylbenzoate, octylpalmitate, octylcocoate, octylisostearate, octyldodeceylmyristate, octyldodecanol, cetearylisononanoate, isopropylmyristate, isopropylpalmitate, isopropylstearate, isopropyloleate, n-butylstearate, n-hexyllaurate, n-decyloleate, isooctylstearate, isononylstearate, isononylisononanoate, 2-ethyl hexyl palmitate, 2-ethylhexyllaurate, 2-hexyldecylstearate, 2-octyldodecylpalmitate, stearylheptanoate, isopropyl lauroyl sarkosinate, oleyloleate, oleylerucate, erucyloleate, erucylerucate, tridecylstearate, tridecyltrimellitate as well as synthetic and semi synthetic and natural mixtures of such esters such as e.g. jojoba oil.

Further particularly suitable oils may be selected from the group of dialkyl ether and dialkylcarbonates such as particularly dicaprylylether (Cetiol OE) and/or dicaprylylcarbonate, (e.g. available as Cetiol CC at Cognis).

Further particularly suitable oils may be selected from the group of isoeikosan, neopentylglykoldiheptanoate, propylenglykoldicaprylaet caprylate/dicaprate, caprylic/capric/diglyceryl succinate, butylene glyckol dicaprylate/dicaprate, $C_{12-13}$-Alkyllactate, Di-$C_{12-13}$-alkyltartrate, triisostearin, dipentaerythrityl hexacaprylate hexacaprate, propylenglykolmonoisostearate, tricaprylin and dimethylisosorbid.

It is particularly advantageous if the oil phase of the topical compositions according to the invention contains an amount of $C_{12-15}$-alkylbenzoate or consists essentially thereof.

Further particularly suitable oily components are e.g. butyloctylsalicylate (e.g. Hallbrite BHB from CP Hall), hexadecylbenzoate and butyloctylbenzoate as well as mixtures thereof (e.g. Hallstar AB).

The topical compositions according to the present invention may also contain apolar oils such as e.g. branched or linear hydrocarbons and waxes, in particular mineral oil, vaseline (Petrolatum), paraffin oil, squalan and squalen, polyolefins, hydrogenated polyisobutenes, $C_{13-16}$ isoparaffin and isohexadecan. Within the group of polyolefins polydecenes are preferred.

Exemplary waxy compounds in particular suitable for the use in the compositions according to the invention are paraffin wax, carnauba wax, beeswax or hydrogenated castor oil.

Exemplary organic solvents in particular suitable for the use in the compositions according to the invention include the lower alcohols and polyols having at most 8 carbon atoms. In particular the compositions according to the invention comprise ethanol in an amount of 5 to 40 wt.-% based on the total weight of the composition.

The thickeners are advantageously selected, in particular, from among the cross linked polyacrylic acids or modified or unmodified guar gums and celluloses, such as hydroxypropylated guar gum, methylhydroxyethylcellulose and hydroxypropylmethylcellulose.

Suitable film forming agents include polymers in the basis of PVP such as in particular copolymers of polyvinylpyrrolidon e.g. PVP hexadecen copolymer and PVP eicosen copolymer which are available as Antaron V216 and Antaron V220 at GAF Chemicals corporations. Further suitable film forming agents include polymeric film formers such as sodiumpolystyrenesulfonate (e.g. Flexan 130 from National Starch and Chemical Corp.) and/or polyisobuten (e.g. Rewopal PIB1000 from Rewo). Further suitable polymers are e.g. polyacrylamide (Seppigel 305), polyvinylalkohole, PVP, PVP/VA copolymers, polyglycols and acrylate/octylacralymid copolymers (e.g. Dermacryl 79). Further suitable is the use of hydrated castor oil dimerdilinoleat (CAS 646054-62-8, INCI Hydrogenated Castor Oil Dimer Dilinoleate), or PPG-3 Benzylethermyristate (CAS 403517-45-3).

The topical compositions according to the invention may further comprise one or several compounds from the group of siloxanes elastomers listed in order to enhance the water resistance and/or enhance the light protection factor such as in particular siloxanes elastomers in the form of spherical powders with the INCI nomenclature Dimethicone/Vinyl Dimethicone Crosspolymer, such as e.g. DOW CORNING 9506 Powder (by Dow corning).

It is particularly advantageous if the siloxane elastomer is used in combination with hydrocarbon oils, synthetic oils, synthetic esters, synthetic ether or mixtures thereof.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The term "topical composition" as used herein refers in particular to a cosmetic composition that can be topically applied to mammalian keratinous tissue, particularly human skin and hair.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Preparations", Verlag für chemische Industrie (ed. H. Ziolkowsky), $4^{th}$ edition, 1992.

Preferred topical compositions according to the invention are skin care preparations, hair care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples for care preparations are hair-washing preparations in the form of shampoos, hair conditioners, hair-care preparations such as e.g. pretreatment preparations, hair tonics, styling creams, gels such as styling gels, pomades, hair rinses, treatment packs, intensive hair treatments, hair-straightening preparations, liquid hair-setting preparations, hair foams (hair mousses) and hairsprays.

Examples of decorative preparations are, in particular, lipsticks, eye shadows, mascaras, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or antimicrobial (antibacterial or antifungal) preparations without being limited thereto.

In a particular embodiment the topical compositions according to the invention are light-protective preparations, such as sun protection milks, sun protection lotions, sun protection creams, sun protection oils, sun blocks or tropical's or day care creams with a SPF (sun protection factor). Of particular interest are sun protection creams, sun protection lotions, sun protection milks and sun protection preparations in the form of a spray or aerosol.

In another particular embodiment the topical compositions are hair-washing preparations in the form of shampoos or hair treatment preparations intended to be left in the hair (and not washed out) such as hair-setting preparations, hairsprays, gels, pomades, styling creams or hair foams (hair mousses), particularly hairsprays, gels or hair foams (hair mousses).

A shampoo may, for example, have the following composition: from 0.01 to 5 wt.-% of a benzotriazole according to the present invention, 12.0 wt.-% of sodium laureth-2-sulfate, 4.0 wt.-% of cocamidopropyl betaine, 3.0 wt.-% of sodium chloride, and water ad 100 wt.-%.

The topical compositions according to the present invention may be in the form of a suspension or dispersion in solvents or fatty substances, or alternatively in the form of an emulsion or micro emulsion (in particular of O/W- or W/O-type, Si/W- or W/Si-type), PIT-emulsion, multiple emulsion (e.g. O/W/O- or W/O/W-type), pickering emulsion, hydrogel, alcoholic gel, lipogel, one- or multiphase solution or vesicular dispersion or other usual forms, which can also be applied by pens, as masks or as sprays. Preferably, the topical compositions are in the form of an emulsion or dispersion.

In one particular embodiment, the topical compositions according to the invention are in the form of an O/W emulsion. If the topical composition according to the invention is an O/W emulsion, then it contains advantageously at least one O/W- or Si/W-emulsifier selected from the list of glyceryl-stearatcitrate, glycerylstearate (self emulsifying), stearic acid, salts of stearic acid, polyglyceryl-3-methylglycosedistearate, ceteareth-20, steareth-2, steareth-12, PEG-40 stearate, Further suitable emulsifiers are phosphate esters and the salts thereof such as cetyl phosphate (Amphisol® A), diethanolamine cetyl phosphate (Amphisol® DEA), potassium cetyl phosphate (Amphisol® K), sodiumcetearylsulfat, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example, PVP eicosene copolymer, acrylates/$C_{10-30}$alkyl acrylate crosspolymer, acrylates/steareth-20 methacrylate copolymer, PEG-22/dodecyl glycol copolymer, PEG-45/dodecyl glycol copolymer, and mixtures thereof. The at least one O/W emulsifier is preferably used in an amount of about 0.001 to 10 wt.-%, more preferably in an amount of 0.1 to 7 wt.-% with respect to the total weigh of the composition. Additionally the topical composition contains advantageously at least one co-emulsifier selected from the list of alkyl alcohols such as Cetyl Alcohol (Lorol C16, Lanette 16) Cetearyl Alcohol (Lanette O), Stearyl Alcohol (Lanette 18), Behenyl Alcohol (Lanette 22), Glyceryl Monostearate, Glyceryl Myristate (Estol 3650), Hydrogenated Coco-Glycerides (Lipocire Na10) without being limited to this and mixtures thereof.

In another particular embodiment, the topical compositions according to the invention are W/O emulsions. If the topical composition according to the invention is a W/O emulsion, then it contains advantageously at least one W/O- or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The topical compositions according to the invention particularly exhibit a pH in the range of 3-10, preferably in the range of pH of 5-8, most preferred in the range of pH 5.5-7.5 which can be adjusted with conventional acids, bases or buffering solutions.

Which amount of the topical composition has to be applied, depends on the concentration of the active ingredient(s) in the product and the desired cosmetic effect(s). A typical "leave-on" composition like a skin care emulsion or light-protective preparation, for example, is usually applied in an amount of about 0.5 to about 2 mg per cm$^2$ skin. The applied amount is normally not critical, and the desired effect(s) may be achieved by using more of the composition, repeating the application of the composition and/or applying a composition which contains more of the active ingredient(s).

By "'leave-on' composition" as used herein a topical composition is meant which after having applied to the skin, is not removed intentionally. It is preferably left on the skin for a period of at least about 15 minutes, more preferably at least about 30 minutes, even more preferably at least about 1 hour, most preferably for at least several hours, e.g. up to about 12 hours.

The topical compositions according to the invention are in particular used for the protection against skin ageing (in particular photo ageing) and as sunscreen.

The following examples are provided to further illustrate the compounds and compositions of the present invention. These examples are illustrative only and are not intended to limit the scope of the invention in any way. The respective formulations are prepared according to methods known to a person skilled in the art.

The names of the ingredients in the following tables are indicated as INCI names. All amounts are given as wt.-% based on the total weight of the composition.

| Gels | 1 | 2 | 3 | 4 | 5 | 6 | 7 | 8 |
|---|---|---|---|---|---|---|---|---|
| Acrylates/Octylacrylamide Copolymer | 1 | 1 | 1 | 1 | 1 | 1 | 1 | 1 |
| Alcohol Denat. | 50 | 62 | 59.2 | 52 | 56 | 59 | 51 | 54 |
| Butylene Glycol Dicaprylate/Dicaprate | | | 7.5 | | | 2 | 4 | |
| C12-15 Alkyl Benzoate | 5 | 8.5 | 5 | 2 | 7.5 | | 2 | 5 |
| Phenylethylbenzoate | 3 | | | 2.5 | | | 2.5 | |
| Cocoglyceride | | | | | | 2 | 5 | |
| Tridecylsalicylate | 2 | 1.5 | | | 3 | 1 | | 3 |
| Hydroxypropoylcellulose | 2 | 0.8 | 1 | 0.8 | 0.5 | 0.8 | 0.45 | 0.5 |
| Butyl Methoxydibenzoylmethane | 4.5 | 4.5 | 2.5 | | 2.5 | 4.5 | | 3 |
| Merocyanine | | | | | 1.8 | | | 5 |
| 2,4,6-Tribiphenyl-4-yl-1,3,5 Triazine | | | | 0.5 | 4 | | 6 | |
| Diethylamino Hydroxybenzoyl Hexyl Benzoate | | | | 4.5 | 3.5 | | | |
| Ethylhexyl Methoxycinnamate | | | 9.5 | | 6.5 | 6.5 | | |
| Ethylhexyl Salicylate | 3 | 4.5 | 4.5 | 4.5 | | | | 5 |
| Homosalate | | | | | | | 4.5 | |
| Octocrylene | 8 | 4.8 | 5.5 | 4.3 | 3.8 | | | 4 |
| Ethylhexyl Triazone | | | | | 2 | | | |
| Benzophenone-3 | 3 | | | | | | | |
| Drometrizole Trisiloxane | | | | 0.5 | 1 | | | 1 |
| Benzotriazole according to the invention such as in particular the compounds of example 2, 3, 4, 5, 6, 7, 12, 13 or 17 | 8.0 | 1.5 | 2.5 | 5 | 3.5 | 2 | 20 | 15 |
| Bis-Ethylhexyloxyphenol Methoxyphenyltriazine | | | | | | 1 | | |
| Benzotriazoyl Dodecyl p-Cresol | | | | | | 5 | | |
| Butyloctyl Methoxycrylene | | | | 4 | | | | |
| Diethylhexyl Syringylidenemalonate | | | 3.8 | | | | | |
| Vitamin E Acetate | | | | | 0.5 | | 0.2 | 0.5 |
| Glycerin | 5 | | 3 | | | | | |
| Ascorbylglucoside | | | 0.1 | | 0.5 | | 1.0 | |
| Fragrance, Colours | | | | q.s | | | | |
| Water | | | | ad 100 | | | | |

| Sprays | 1 | 2 | 3 | 4 | 5 | 6 | 7 | 8 | 9 | 10 | 11 | 12 |
|---|---|---|---|---|---|---|---|---|---|---|---|---|
| Acrylates/Octylacrylamide Copolymer | 1 | | | | 1 | 1 | | 1 | | | 1 | |
| VP/VA Copolymer | | 1 | | 0.5 | | | | 0.5 | | | | 0.5 |
| Alcohol Denat. | 42 | 57 | 60 | 53 | 35.5 | 43.5 | 40 | 53 | 35.5 | 20 | 34 | 53 |
| Potassium Cetyl Phosphate | | | | | | | | | | 2 | 3 | |
| Cetearyl Alcohol | | | | | | | | | | 0.2 | | |
| Cetyl Alcohol | | | | | | | | | | | 0.3 | |
| Acrylates/C10-30 Alkyl Acrylate Crosspolymer | | | | | | | | | | 0.2 | 0.15 | |
| Cyclomethicone | 4.9 | 2 | 5 | 0.5 | 8 | 8 | 3 | 0.5 | 10 | 4 | 10 | 0.5 |
| Tridecylsalicylate | 0.5 | 2.5 | 4 | 7 | 10 | 3 | 3 | 7 | 4 | 0.5 | 4 | 7 |
| Bis-Ethylhexyloxyphenol Methoxyphenyltriazine | | | | | 1 | | | | 1 | | 1 | |
| Ethylhexyl Bis-Isopentylbenzoxazolyl phenyl Melamine | 0.5 | | 1 | | | 3 | | | | | | |
| Butyl Methoxy-dibenzoylmethane | 4.5 | 2 | | 3 | 5 | | | 3 | 3-5 | 4 | 3 | 3 |
| Diethylamino Hydroxybenzoyl Hexyl Benzoate | | 2 | 3 | | | 4.5 | | | | 7.5 | | |
| Ethylhexyl Methoxycinnamate | | | | 7 | | | 8.5 | 7 | | 7.5 | | |
| Ethylhexyl Salicylate | 4.5 | 3.5 | 2 | 4 | 4.5 | 1.5 | | 4 | 5 | | 4 | 4 |
| Drometrizole Trisiloxane | | 0.5 | | | | 1 | | | | 2 | | |
| 2,4,6-Tribiphenyl-4-yl-1,3,5 Triazine | 1 | | | 5 | | | | 2 | | | | 2 |
| Merocyanine | | | 3 | | | 0.5 | | | | 2 | | |
| Methylene Bis-Benztriazoyl Tetramethylbutylphenol | | | | | | | | 3 | | | | |
| 1,1'-(1,4-piperazinediyl)bis[1-[2-[4-(diethylamino)-2-hydroxybenzoyl] phenyl]-methanone | | | | | | | | | | | | 3 |
| Homosalate | 9.5 | 5 | 3 | | 5.5 | | | 15 | 5 | | 7 | |
| Octocrylene | 9.5 | | 8 | | 7.5 | 8.5 | | | 10 | | | |

| Sprays | 1 | 2 | 3 | 4 | 5 | 6 | 7 | 8 | 9 | 10 | 11 | 12 |
|---|---|---|---|---|---|---|---|---|---|---|---|---|
| Benzotriazole according to the invention such as in particular the compounds of example 2, 3, 4, 5, 6, 7, 12, 13 or 17 | 3 | 2.5 | 6.8 | 1 | 4 | 2 | 20 | 10 | 3 | 15 | 20 | 10 |
| Phenylbenzimidazole Sulfonic Acid | | | | | 2 | | | | 0-3 | | | |
| Polysilicone-15 | | 1.5 | | | 2 | | | | 0.99 | | | |
| Methylbenzylidene Camphor | | 1 | | | | | | | | | | |
| Butylene Glycol Dicaprylate/Dicaprate | | 9 | | | | | | | | 2 | | |
| $C_{12-15}$ Alkyl Benzoate | | 2 | | 2 | | | | 2 | 5 | | 5 | 2 |
| Phenylbenzoate | | | 7 | | 4 | | 7 | | 4 | | 4 | |
| Benzotriazoyl Dodecyl p-Cresol | | | | | | | | 3 | | | | 3 |
| Butyloctyl Methoxycrylene | | | | | | | | | | 4 | | |
| Diethylhexyl Syringylidenemalonate | | 2 | | | | | | | | | | |
| Diethylhexylnaphthalate | | 6 | | 3 | | | | 3 | | | | 3 |
| Isopropyl Lauroyl Sarcosinate | 2 | | 1 | | 3 | | 1 | | 3 | | 3 | |
| Phenyl Trimethicone | 2 | 5 | | | 1 | 2 | | | 1 | 2 | 1 | |
| Octyldodecanol | | | | 8 | | | | 8 | | | | 8 |
| Glycerin | 5 | 4 | 5 | 8 | 5 | 5 | 5 | 8 | 5 | 5 | 5 | 8 |
| Vitamine E Acetate | 0.1 | | 0.5 | | | | 0.5 | | | | | |
| Fragrance, Colours | | | | | | | q.s | | | | | |
| Water | | | | | | | Ad 100 | | | | | |

| O/W Emulsions | 1 | 2 | 3 | 4 | 5 | 6 | 7 | 8 | 9 | 10 |
|---|---|---|---|---|---|---|---|---|---|---|
| Glyceryl Stearate Citrate | 2 | 2 | 3 | | | | | | | 3 |
| Glyceryl Stearate SE | | | | 1 | 1 | 1.5 | | | 1.5 | |
| Cetearyl Alcohol + PEG-40 Rizinusoil + Sodium Cetearyl Sulfate | | | | 2.5 | 2.5 | 3 | | | | |
| Potassium Cetyl Phosphate | | | | | | | 2 | 2 | 1.5 | |
| Cetearyl Alcohol | | | 1 | 1 | | | 2 | 2 | 0.5 | 1 |
| Stearyl Alcohol | 0.5 | | | | | 2 | | | 0.5 | |
| Myristyl Myristate | 1 | 1 | | | 3 | | | 2 | | |
| Acrylates/$C_{10-30}$ Alkyl Acrylate Crosspolymer | 0.1 | 0.2 | | | 0.1 | | | 0.2 | | |
| Carbomer | | 0.2 | 0.3 | 0.2 | | | | | | 0.3 |
| Xanthan Gum | 0.4 | | 0.2 | 0.2 | 0.3 | 0.4 | 0.2 | | 0.3 | 0.2 |
| $C_{12-15}$ Alkyl Benzoate | | 3 | | | 5 | | 4 | 5 | | |
| 2-Phenylethylbenzoate | 5 | 2 | | | | | | | | |
| Butylene Glycol Dicaprylate/Dicaprate | 5 | | | | 3 | 3 | | | 7.5 | 3 |
| Tridecylsalicylate | 1.5 | 2.5 | 0.25 | 5.9 | 7 | 15 | 5.9 | 7 | 6 | 0.25 |
| Dicaprylcaprate | 2 | 2 | | | 2 | 2 | | 2 | 2 | |
| Cyclomethicone | | | | 5 | 10 | | 5 | | | |
| Dimethicone | | | | | 5 | | | 5 | | |
| PVP Hexadecene Copolymer | | 0.5 | | | | 1 | 2 | | 1 | |
| Propylene Glycol | | | 1 | | 5 | 3 | | | 3 | 1 |
| Ascorbylglucoside | | 0.1 | | | 0.5 | | | | 1.0 | |
| Glycerin | 3 | 5 | 7 | 10 | 13 | 3 | 3 | 5 | 3 | 7 |
| Alcohol denat. | 2 | 3 | | 7 | | | | | | |
| Merocyanine | 1 | | | | 3 | | 0.8 | | | |
| Titanium Dioxide | 3 | | | 2 | | | 3 | | | |
| Phenylene-1,4-bis-(2-benzimidazyl)-3,3-5,5-tetrasulfonic Acid | 3 | 2 | | | | | | | | |
| Ethylhexyl Triazone | 2.5 | 2 | | 1 | | | 1 | | | |
| Phenylbenzimidazole Sulfonic Acid | | | 2 | | | 1 | 2 | | 1 | 2 |
| 4-Methoxycinnamate (2-ethylhexyl) ester | | 5 | | 2 | | | | | | |
| Butyl Methoxydibenzoylmethane | 5 | 1 | | | 3 | | 4 | | 5 | |
| Ethylhexylsalicylate | 5 | | 0.5 | 4 | 5 | | 4 | | | 0.5 |
| Polysilicone-15 | | | 4 | | | | 1 | | | 4 |
| Isoamyl p-Methoxycinnamate | | 3 | 6 | | | | | | | 6 |
| Diethylamino Hydroxybenzoyl Hexyl Benzoate | | | | | 6 | | | | 3 | |
| Methylene Bis-Benztriazoyl Tetramethylbutylphenol | | | 5 | | | | | | | |
| 1,1'-(1,4-piperazinediyl)bis[1-[2-[4-(diethylamino)-2-hydroxybenzoyl] phenyl]-methanone | | | | | | | | | | 5 |
| Ococtcrylene | 3 | | | 5 | | 7 | 4 | | 7 | |
| Bis-Ethylhexyloxyphenol Methoxyphenyltriazine | | 1 | | 1 | | 1 | 0.5 | | 1 | |
| Benzotriazole according to the invention such as in particular the compounds of example 2, 3, 4, 5, 6, 7, 12, 13 or 17 | 10 | 1 | 4 | 6 | 3 | 5 | 20 | 20 | 15 | 4 |
| Benzotriazoyl Dodecyl p-Cresol | | 0.9 | | | | | | | | |
| Butyloctyl Methoxycrylene | | | | | 3 | | | | | |
| Diethylhexyl Syringylidenemalonate | | | | | | | | 2 | | |
| Vitamine E Acetat | 0.2 | 0.2 | 0.2 | 0.3 | 0.1 | 0.5 | 0.3 | 0.1 | 0.5 | 0.2 |
| Disodium EDTA | 0.1 | 0.1 | 0.2 | 0.2 | 0.5 | 0.2 | 0.2 | 0.2 | 0.2 | 0.2 |
| Fragrance, Preservation agents | q.s | q.s | q.s | q.s | q.s | q.s | q.s | q.s | q.s | q.s |

-continued

| | | | | | | | | | | |
|---|---|---|---|---|---|---|---|---|---|---|
| Colours, etc. | q.s | q.s | q.s | q.s | q.s | q.s | q.s | q.s | q.s | q.s |
| Citric Acid, Sodium Citrate | q.s | q.s | q.s | q.s | q.s | q.s | q.s | q.s | q.s | q.s |
| Sodium Hydroxide | q.s | q.s | q.s | q.s | q.s | q.s | | q.s | | q.s |
| Tromethamine | | | | | | | q.s | | q.s | |
| Water | | | | | | ad 100 | | | | |

| O/W Emulsions | 11 | 12 | 13 | 14 | 15 | 16 | 17 | 18 | 19 |
|---|---|---|---|---|---|---|---|---|---|
| Glyceryl Stearate | 2.5 | 2 | 1.2 | 1 | | | 1 | 1 | |
| PEG-40 Stearate | 1 | | | | | | | | |
| PEG-100 Stearate | | 2.5 | | | | | | 1 | |
| Ceteareth-20 | | | | | 1 | | | | |
| Glyceryl Stearate Citrate | | | | | | 0.5 | | | 0.5 |
| Potassium Cetyl Phosphate | | | | | | | 3 | 1.5 | 2 |
| Stearic Acid | | | 2.5 | 3 | | | | | |
| Cetearyl Alcohol | 4 | | | 2 | | | 2 | | |
| Stearyl Alcohol | | 2 | 1 | | | | | | |
| Cetyl Alcohol | | | 1 | 1 | | | | 0.5 | |
| Acrylates/C$_{10-30}$ Alkyl Acrylate Crosspolymer | | | | 0.2 | 0.2 | 0.4 | 0.2 | | 0.4 |
| Carbomer | 0.1 | | 0.2 | | | | | | |
| Xanthan Gum | | 0.3 | | | | | | 0.3 | |
| C$_{12-15}$ Alkyl Benzoate | 5 | | | 2 | 5 | 5 | 10 | 5 | 5 |
| Vaseline | 5 | | 3 | | | | | | |
| Butylene Glycol Dicaprylate/Dicaprate | | 4 | 2 | | 9 | | | 9 | |
| Hydrogenated Polydecene | | | 3 | | 2 | | | 2 | |
| Caprylic/Capric Triglyceride | 1 | 3 | | 5 | | 5 | 5 | | 5 |
| Cyclomethicone | | 5 | 2 | | | 10 | | | 10 |
| Methylpropandiol | 2 | | | | 3 | | | 3 | |
| Isopropyl Lauroyl Sarcosinate | | | | | | | | | |
| Glycerine | 7.5 | 10 | 4 | 5 | 5 | | 5 | 5 | |
| Alcohol denat. | 1 | 3 | 0.5 | 10 | 4 | 8 | | 4 | 8 |
| Butylene Glycol | | | 3 | | | | | | |
| Ascorbylglucoside | | 0.5 | | 1.0 | | 1.5 | | 0.1 | |
| Isotridecylsalicylate | | | 1 | 3 | 5 | 2 | 3 | 5 | |
| Titanium Dioxide | 1 | | 0.5 | 2 | | | | | 5 |
| Merocyanine | | | | | 1.8 | | | 5 | |
| 2,4,6-Tribiphenyl-4-yl-1,3,5 Triazine | | | 0.5 | 4 | | 6 | | | |
| Ethylhexyl Bis-Isopentylbenzoxazolylphenyl Melamine | | 1 | | | 0.5 | | | 2 | |
| Ethylhexyl methoxycinnamate | | | | | 2 | | | | |
| Phenylbenzimidazole Sulfonic Acid | 1.5 | | | 2 | | 2 | 0-2 | | |
| Butyl Methoxydibenzoylmethane | 2.5 | 1 | | 2 | 2 | 3 | 3-5 | 3 | |
| Methylbenzylidene Camphor | | | | | 2 | 3 | | | |
| Disodium Phenyl Dibenzimidazole Tetrasulfonic Acid | | | | | | | | | 2 |
| Benzotriazole according to the invention such as in particular the compounds of example 2, 3, 4, 5, 6, 7, 12, 13 or 17 | 1.5 | 1 | 4 | 3 | 5 | 3 | 3 | 20 | 16 |
| Ocotcrylene | | 5 | | | | 2 | 10 | | 2 |
| Polysilicone-15 | | | | | 2 | 3 | | | |
| Ethylhexyl Salicylate | 3 | | | | 5 | | 5 | | |
| Homosalate | | | | 4 | 2 | | 15 | | 3 |
| Benzophenone-3 (Oxybenzone) | | | | | | 6 | | | |
| Drometrizole Trisiloxane | 0.5 | | | 1 | | 2 | | | |
| Terephthalidene Dicamphor Sulfonic Acid | 1.5 | | | 0.5 | | 0.25 | | | |
| Benzotriazoyl Dodecyl p-Cresol | 3 | | | | | | | | |
| Butyloctyl Methoxycrylene | | | | | | 2 | | | |
| Tapioca Starch | 1 | | 2.5 | | | 0.5 | | | 0.5 |
| Sodium Starch Octenylsuccinate | | | | | 1 | | 1 | | |
| Disodium EDTA | 0.1 | | | | | 0.5 | | | 0.5 |
| Fragrance, Preservatives | q.s | q.s | q.s | q.s | q.s | q.s | q.s | q.s | q.s |
| Sodium Hydroxide | q.s | q.s | q.s | q.s | q.s | q.s | q.s | q.s | q.s |
| Water | | | | | | Ad 100 | | | |

| W/O Emulsion | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Polyglyceryl-2 Dipolyhydroxystearate | 3 | 5 | 3 | | | | | | 5 | 5 | 5 | 3 | 3 | |
| PEG-30 Dipolyhydroxystearate | | | 2 | 3 | 4 | 5 | 3 | 4 | | | | 2 | | 4 |
| Sodium Starch Octenylsuccinate | 0.5 | 0.4 | 0.6 | 0.3 | 0.5 | 1 | 0.3 | 0.5 | 1 | 0.5 | 1 | 0.5 | 0.6 | 0.5 |
| Glycine | 0.3 | 0.3 | 0.5 | 0.4 | | | 0.4 | | | | | 0.3 | 0.5 | |
| Alcohol denat. | 2 | 5 | 2 | 0.5 | 8 | 1 | | 8 | 5 | | 3 | 2 | 2 | 8 |
| Magnesium Sulfate | 0.2 | 0.3 | 0.3 | 0.4 | 0.5 | 0.2 | 0.5 | 0.5 | 0.5 | 0.5 | 0.5 | 0.2 | 0.3 | 0.5 |
| C12-15 Alkyl Benzoate | 5 | 3 | | | 5 | | | 5 | | 4 | | 5 | | 5 |
| Triheptanoin | | 2 | | | | | | | | | | | | |
| Butyleneglycol Dicaprylat/Dicaprate | 5 | | | 3 | 3 | | 3 | | 3 | 6 | 3 | 5 | | 3 |
| Dicaprylyl Ether | | | | | 2 | | | 2 | | 2 | | | | 2 |
| Mineral Oil | | 4 | | 6 | | 8 | 6 | | 8 | | 8 | | | |
| Octyldodecanol | 2 | | | | | | | | | | | 2 | | |
| Dicapryl Caprate | | 2 | | | 2 | 2 | | 2 | 2 | 2 | 2 | | | 2 |

| W/O Emulsion | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Cyclomethicone | 5 |  | 5 | 10 |  |  |  |  |  |  |  | 5 | 5 |  |
| Dimethicone |  |  |  | 5 |  |  | 5 |  |  |  |  |  |  |  |
| Isohexadecane |  | 1 |  |  |  |  |  |  |  |  |  |  |  |  |
| Butylene Glycole | 5 | 8 |  |  |  | 3 |  |  | 3 |  | 3 | 5 |  |  |
| Glycerin | 3 | 5 | 7 | 10 | 3 | 3 | 10 | 3 | 3 | 3 | 3 | 3 | 7 | 3 |
| Tridecylsalicylate |  | 1 | 2 |  |  | 0.5 |  |  | 0.5 |  | 0.5 | 2 |  |  |
| 2-Phenylethylbenzoate |  |  | 2 |  | 4 |  |  | 4 |  |  |  | 2 | 1 | 2 |
| Isopropyl Lauroyl Sarcosinate |  |  | 1 |  | 2 |  |  | 2 |  |  |  |  |  |  |
| Ethylhexylmethoxycinnamate | 2 |  |  |  |  |  |  | 5 |  |  |  | 5 | 7 | 5 |
| Ethylhexyl Triazone | 2 | 3 | 3 |  |  | 3 |  |  |  |  | 1 | 2 | 3 |  |
| Ethylhexyl Bis-Isopentyl-benzoxazolylphenyl Melamine |  |  |  | 3 |  |  |  | 0.5 |  |  |  |  |  |  |
| Diethylhexyl Butamido Triazone |  | 1.5 | 1.5 |  |  | 1.5 |  |  |  |  |  |  | 1.5 |  |
| Butyl Methoxy dibenzoylmethane | 1 | 4 | 3 |  | 5 | 2.5 | 2 | 5 |  | 2 | 3 |  |  |  |
| Methylbenzylidene Camphor |  |  |  |  | 1 |  |  |  |  |  | 2 |  |  |  |
| 2,4,6-Tribiphenyl-4-yl-1,3,5 Triazine |  |  | 5 |  |  |  |  | 2 |  |  |  |  | 5 |  |
| Merocyanine |  |  |  |  | 3 |  |  |  |  | 2 |  |  |  | 3 |
| 2-(4-Diethylamino-2-hydroxybenzoyl)-Benzoic Acid Hexylester |  |  |  | 2 |  |  |  | 1 |  |  |  |  |  |  |
| Benzotriazole according to the invention such as in particular the compounds of example 2, 3, 4, 5, 6, 7, 12, 13 or 17 | 2 | 4 | 3 | 0.75 | 5 | 2.5 | 10 | 15 | 20 | 15 | 10 | 2 | 4 | 5 |
| Titanium Dioxide (Parsol TX) | 5 | 4 | 2 |  | 3 | 4 |  | 3 |  | 3 | 4 | 5 | 2 | 3 |
| Polysilicone-15 | 2 |  |  |  | 1.5 | 2 |  |  |  | 3 |  |  |  |  |
| Octocrylene |  | 3.6 |  |  |  |  | 2 |  | 5 | 2 |  |  |  |  |
| Ethylhexyl Salicylate |  |  |  |  | 5 |  |  |  |  |  |  |  |  |  |
| Phenylbenzimidazole Sulfonic Acid | 3 |  |  |  |  |  | 1 |  |  | 2 |  |  |  |  |
| Bis-Ethylhexyloxyphenol Methoxyphenyltriazine | 1 | 2 | 2 |  | 2 | 3 |  |  |  | 1.5 |  | 1 | 2 | 2 |
| Methylene Bis-benzotriazolyl tetramethylbutylphenol | 2 |  | 3 |  | 1 |  |  |  |  |  | 1 |  |  |  |
| 1,1'-(1,4-piperazinediyl)bis[1-[2-[4-(diethylamino)-2-hydroxybenzoyl] phenyl]-methanone |  |  |  |  |  |  |  |  |  |  |  | 2 | 3 | 1 |
| Benzotriazoyl Dodecyl p-Cresol |  |  |  |  |  |  |  |  |  | 3 |  |  |  |  |
| Butyloctyl Methoxycrylene |  | 4 |  |  |  |  |  |  |  |  |  |  | 4 |  |
| Vitamin E Acetate | 0.2 | 0.2 | 0.2 | 0.3 | 0.1 | 0.5 | 0.3 | 0.1 | 0.5 | 0.1 | 0.5 | 0.2 | 0.2 | 0.1 |
| Ascorbylglucoside | 0.2 |  | 0.5 |  |  |  | 1.0 |  |  | 2.0 |  |  |  |  |
| Disodium EDTA | 0.1 | 0.1 | 0.2 | 0.2 | 0.2 | 0.5 | 0.2 | 0.2 | 0.5 | 0.2 | 0.5 | 0.1 | 0.2 | 0.2 |
| Fragrance, Preservatives | q.s | q.s | q.s | q.s | q.s | q.s | q.s | q.s | q.s | q.s | q.s | q.s | q.s | q.s |
| Water |  |  |  |  |  |  | ad 100 |  |  |  |  |  |  |  |

| Hydrodispersions | 1 | 2 | 3 | 4 | 5 | 6 | 7 | 8 |
|---|---|---|---|---|---|---|---|---|
| Glyceryl Stearate Citrate |  |  | 0.4 |  |  |  |  |  |
| Sodium Carbomer |  |  |  |  | 0.3 |  |  |  |
| Acrylates/C$_{10-30}$ Alkyl Acrylate Crosspolymer |  |  | 0.3 | 0.4 | 0.1 | 0.1 | 0.2 | 0.1 |
| Ceteareth-20 |  |  | 1 |  |  |  |  |  |
| Potassium Cetyl Phosphate |  |  |  |  | 2 |  |  | 2 |
| Xanthan Gun | 0.5 |  |  | 0.15 |  | 0.5 | 0.2 | 0.2 |
| Dimethicone/Vinyl Dimethicone Crosspolymer |  |  |  |  | 5 |  | 3 | 1.5 |
| 2-(4-Diethylamino-2-hydroxybenzoyl)-benzoic Acid Hexylester |  |  |  | 0.5 | 2 | 1.5 |  | 1.5 |
| 2,4,6-Tribiphenyl-4-yl-1,3,5 Triazine |  |  |  |  |  | 3 | 0.5 |  |
| Merocyanine |  | 2 |  |  |  |  |  | 4 |
| Butyl Methoxydibenzoylmethane |  | 2 |  | 3.5 | 2 | 3 | 5 | 2 |
| Ethylhexyl Bis-Isopentylbenzoxazolylphenyl Melamine |  |  |  | 0.5 |  |  | 2 |  |
| Bis-Ethylhexyloxyphenol Methoxyphenyltriazine |  |  | 2 |  | 0.25 |  |  | 1 |
| Disodium Phenyl Dibenzimidazole Tetrasulfonate |  | 2 |  |  |  | 1 |  |  |
| Phenylbenzimidazole Sulfonic Acid |  |  | 1 | 2 |  |  |  | 0.5 |
| Ethylhexyl Methoxycinnamate |  |  |  |  |  | 8 |  |  |
| Ethylhexyl Salicylate |  |  |  |  | 4 |  |  |  |
| Homosalate |  |  |  |  | 10 |  |  |  |
| Diethylhexyl Butamido Triazone |  |  |  | 2 | 2 |  |  |  |
| Ethylhexyl Triazone |  | 4 | 3 |  | 4 |  | 1 | 1 |
| Octocrylene |  | 2 |  | 1 |  |  |  |  |
| Polysilicone-15 |  |  | 0.9 |  |  |  |  | 3 |
| Methylbenzylidene Camphor |  |  |  | 3 |  |  | 2 |  |
| Benzotriazole according to the invention such as in particular the compounds of example 2, 3, 4, 5, 6, 7, 12, 13 or 17 | 1 | 5 | 3 | 3 | 3 | 8 | 10 | 15 |

| Hydrodispersions | 1 | 2 | 3 | 4 | 5 | 6 | 7 | 8 |
|---|---|---|---|---|---|---|---|---|
| Titanium Dioxide | 0.5 | 2 | 1 | 2 | 0-3 | 1 | 2 | |
| Drometrizole Trisiloxane | | | | | 1 | 0.5 | | |
| Terephthalidene Dicamphor Sulfonic Acid | | | | 0.5 | | 0.75 | | |
| Benzotriazoyl Dodecyl p-Cresol | | | 3 | | | | 8 | |
| $C_{12-15}$ Alkyl Benzoate | 2 | | 2.5 | | | | | 7.5 |
| Butylene Glycol Dicaprylate/Dicaprate | 4 | | | | 6 | | | |
| Dicaprylyl Carbonate | | 3 | | | | | | 1.5 |
| Dicaprylylether | | 2 | | | | | | |
| Cyclomethicone | | | | | 7.5 | | 3 | |
| 2-Phenylethylbenzoate | | | | 4 | | 2 | | |
| Diethylhexylnaphthalate | 5 | | 6 | | | | | |
| Tridecylsalicylate | 2 | 3 | 1 | 5 | 3 | 0.5 | 3 | |
| PVP Hexadecene Copolymer | 0.5 | | 0.5 | | 0.5 | 1 | | |
| Glycerin | 10 | 5 | 5 | | 5 | 8 | | 3 |
| Butylene Glycol | | 7 | | | | | | |
| Glycine Soja | | | | 1 | | | 1 | |
| Vitamin E Acetate | 0.5 | 0.25 | 0.5 | 0.25 | 0.75 | 1 | 0.25 | 0.5 |
| Alpha-Glycosylrutin | | | | | 0.25 | | | |
| Trisodium EDTA | | 0.1 | 0.1 | 0.1 | 0.2 | | 0.1 | 0.1 |
| Tromethamine | | | q.s. | | | | | q.s. |
| Ethanol | 3 | 10 | 4 | 3.5 | 0.5 | 1 | | |
| Preservatives | q.s | q.s | q.s | q.s | q.s | q.s | q.s | q.s |
| Fragrance, Colours | q.s | q.s | q.s | q.s | q.s | q.s | q.s | q.s |
| Water | | | | Ad 100 | | | | |

| Foams | 1 | 2 | 3 | 4 | 5 | 6 |
|---|---|---|---|---|---|---|
| Stearic Acid | 2 | 2 | | | | |
| Palmitic Acid | | | 1.5 | | 1.5 | 1.5 |
| Cetyl Alcohol | 2.5 | 2 | | 2 | | |
| Potassium Cetyl Phosphate | | | | 2 | 1.5 | 1.5 |
| Stearyl Alcohol | | | 3 | | 3 | 3 |
| PEG-100 Stearate | | | | 3.5 | | |
| PEG-40 Stearate | | 2 | | | | |
| PEG-20 Stearate | 3 | | | | | |
| Sorbitan Stearate | | | 0.8 | | 0.5 | |
| $C_{12-15}$ Alkyl Benzoate | 5 | | | | | 8 |
| $C_{12-13}$ Alkyl Tartrate | | | 7 | | 7 | |
| Butyleneglycol Dicaprylate/Dicaprate | | | 6 | 5 | | |
| Dicaprylyl Ether | | | | 2 | 2 | 2 |
| Cyclomethicone | | | 2 | 3 | 3 | 2 |
| Butylene Glycol | 1 | | | | | 3 |
| Isohexadecane | 2 | | | | | |
| Methylpropandiol | | | | | | |
| Propylene Glycol | | | 5 | | 5 | |
| Glycerin | 5 | 7 | | 3 | | |
| 2-(4-Diethylamino-2-hydroxybenzoyl)-Benzoic Acid Hexylester | 2 | | | | | |
| Merocyanine | | | | | | 2.4 |
| Butyl Methoxydibenzoylmethane | | 3 | 2 | | 3 | 4 |
| Dimethicodiethylbenzalmalonate | | | 3 | | | |
| Homosalate | | | 5 | | | 5 |
| Phenylbenzimidazole Sulfonic Acid | | | 2 | 2 | | |
| Benzophenone-3 | 2 | | | | | |
| Ethylhexyl Salicylate | | | 5 | | 3 | |
| Octocrylene | 2 | | | 3 | | 2 |
| Bis-Ethylhexyloxyphenol Methoxyphenyltriazine | | | 3 | 1 | | |
| 2,2 Methylen-bis-(6(2H-benzotriazol-2-yl)-4-(1,1,3,3-tetramethylbutyl)phenol | | | | 8 | | |
| 2,4,6-Tribiphenyl-4-yl-1,3,5 Triazine | 5 | | | 0.5 | | |
| Benzotriazole according to the invention such as in particular the compounds of example 2, 3, 4, 5, 6, 7, 12, 13 or 17 | 3 | 3 | 6 | 15 | 20 | 10 |
| $C_8$-$C_{16}$ Alkylpolyglycoside | 1 | | | | | |
| Vitamin E Acetate | 0.6 | 0.5 | 0.2 | 0.5 | 0.2 | 0.2 |
| Creatine/Creatinine | | | 0.5 | | 0.5 | 0.5 |
| BHT | | | 0.1 | | 0.1 | 0.1 |
| Disodium EDTA | 0.5 | | | | | |
| Fragrance, Preservatives | q.s | q.s | q.s | q.s | q.s | q.s |
| Colours | q.s | q.s | q.s | q.s | q.s | q.s |
| Sodium Hydroxide | q.s | | | | q.s | q.s |
| Potassium Hydroxide | | | | | q.s | |
| Tromethamine | | | q.s | q.s | | |
| Water | | | ad 100 | | | |

EXAMPLE 1

2-(2H-Benzotriazol-2-yl)-6-chloromethyl-4-methyl-phenol

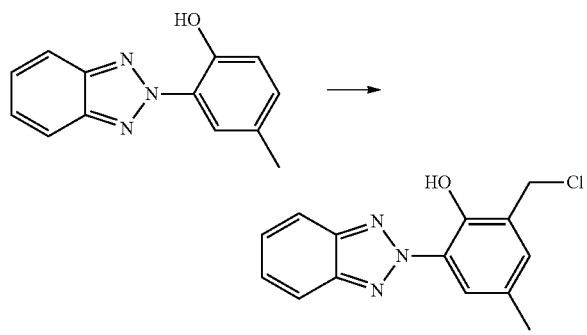

2-(2H-Benzotriazol-2-yl)-4-methyl-phenol (2.3 g, 10 mmol) is dissolved in acetic acid (30 mL) at 80° C. Zinc chloride (140 mg, 1 mmol) and paraformaldehyde (390 mg, 13 mmol) are added and HCl gas is passed through the reaction mixture for 12 hours at 80° C. The product, which precipitates after cooling to room temperature, is filtered off, washed with small amounts of cold ethyl acetate and dried at 60° C. under vacuum to yield 1.9 g of 2-(2H-benzotriazol-2-yl)-6-chloromethyl-4-methyl-phenol.

EXAMPLE 2

2-(2H-Benzotriazol-2-yl)-6-(2-ethylhexyloxymethyl)-4-methyl-phenol

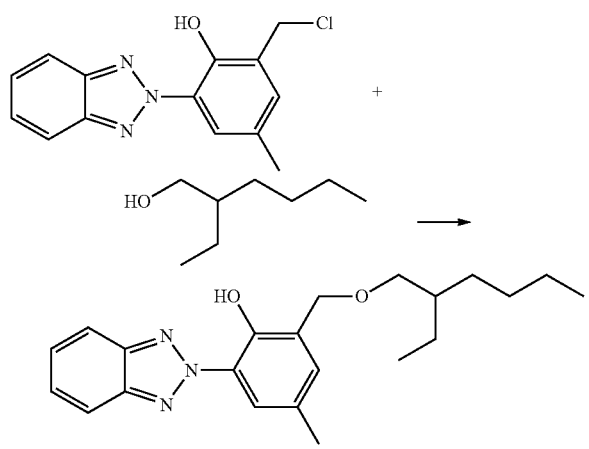

a.) 2-(2H-Benzotriazol-2-yl)-6-chloromethyl-4-methyl-phenol (1.0 g, 3.7 mmol) is partly solved in tetrahydrofurane (20 mL) at 70° C. 2-Ethyl-hexan-1-ol (9.6 g, 73 mmol), potassium tert.butylate (1.0 g, 7.3 mmol), and a catalytic amount of potassium iodide are added subsequently. The orange reaction mixture is stirred at 70° C. for one hour and evaporated to dryness. The residue is dissolved in ethyl acetate and extracted with water. The organic layer is dried over sodium sulphate, filtered and evaporated to dryness. Excess alcohol is removed and recovered by distillation. The crude product is purified by column chromatography (ethyl acetate/heptane 1:12) to yield 1.2 g of 2-(2H-Benzotriazol-2-yl)-6-(2-ethylhexyloxymethyl)-4-methyl-phenol.

b.) 2-(2H-benzotriazol-2-yl)-6-chloromethyl-4-methyl-phenol (0.5 g, 1.9 mmol) is suspended in 2-ethylhexan-1-ol (5.0 g, 38 mmol) at 60° C. 1.1 equivalent $K_2HPO_4$ is added and the mixture is stirred for 12 hours at 60° C. resulting in 63.3% of 2-(2H-Benzotriazol-2-yl)-6-(2-ethylhexyloxymethyl)-4-methyl-phenol (determined by means of HPLC analysis).

c.) 2-(2H-Benzotriazol-2-yl)-6-chloromethyl-4-methylphenol (1.0 g, 3.7 mmol) is suspended in 2-ethylhexan-1-ol (4.0 g, 31 mmol) at 80° C. 1.1 equivalent of the respective base as given in table 1 is added and the mixture is stirred for 15 minutes at 80° C. The turnover and impurity profile is determined by means of HPLC analysis.

In case of sodium methoxide (NaOMe, entry 5) the base is first combined with 2-ethylhexan-1-ol and methanol is removed by distillation under vacuum at 80° C. Subsequently 2-benzotriazol-2-yl-6-chloromethyl-4-methyl-phenol is added and the reaction mixture is stirred 15 minutes at 80° C.

TABLE 1

| entry | base | Turnover* | side products# |
|---|---|---|---|
| 1 | $Na_2CO_3$ | 100% | 4.4% benzylalcohol derivative |
| 2 | $Li_2CO_3$ | 100% | 0.4% |
| 3 | $K_2CO_3$ | 100% | 3.0% |
| 4 | Na | 100% | ~0.5-1% oligomers |
| 5 | NaOMe | 100% | 0.5% benzylalcohol derivative & ~0.5-1% oligomers |
| 6 | NaH | 100% | ~0.5-1% oligomers |
| 7 | tBuOK | 100% | 1.0% |

*i.e. total consumption of 2-(2H-benzotriazol-2-yl)-6-chloromethyl-4-methyl-phenol
i.e. amount of side products detected

EXAMPLE 3

2-(2H-Benzotriazol-2-yl)-4-methyl-6-(3,5,5-trimethylhexyloxymethyl)-phenol

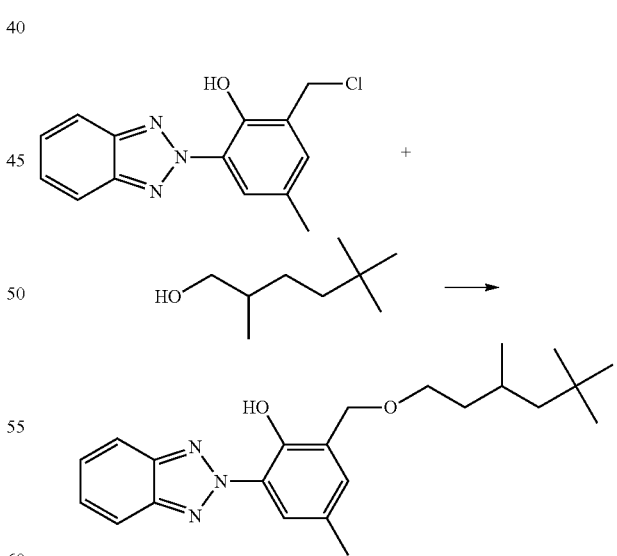

2-(2H-Benzotriazol-2-yl)-6-chloromethyl-4-methyl-phenol (7.0 g, 25.6 mmol) is partly solved in dioxane (190 mL) at 80° C. 3,5,5-Trimethyl-hexan-1-ol (124.1 g, 731 mmol) and sodium hydride (1.7 g, 42 mmol, 60% in mineral oil) are added subsequently. The orange reaction mixture is stirred at 80° C. for one hour and evaporated to dryness. The residue is dissolved in ethyl acetate and extracted with water. The organic layer is dried over sodium sulphate, filtered and evaporated to dryness. The crude product is purified by column chromatography (ethyl acetate/heptane 1:12) to yield 4.8 g of 2-(2H-Benzotriazol-2-yl)-4-methyl-6-(3,5,5-trimethylhexyloxymethyl)-phenol.

EXAMPLE 4

2-(2H-Benzotriazol-2-yl)-6-(3,3,5-trimethyl-cyclohexyloxymethyl)-4-methyl-phenol

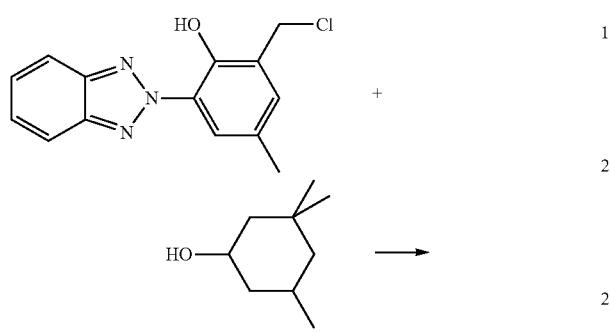

2-(2H-Benzotriazol-2-yl)-6-chloromethyl-4-methyl-phenol (0.8 g, 2.9 mmol) is partly solved in dioxane (23 mL) at 80° C. 3,3,5-Trimethyl-cyclohexanol (12.3 g, 86 mmol) and sodium hydride (200 mg, 5 mmol, 60% in mineral oil) are added subsequently. The orange reaction mixture is stirred at 70° C. for one hour and evaporated to dryness. The residue is dissolved in ethyl acetate and extracted with water. The organic layer is dried over sodium sulphate, filtered and evaporated to dryness. The crude product is purified by column chromatography (ethyl acetate/heptane 1:4) to yield 0.8 g of 2-(2H-Benzotriazol-2-yl)-6-(3,3,5-trimethyl-cyclohexyloxymethyl)-4-methyl-phenol.

EXAMPLE 5

2-(2H-Benzotriazol-2-yl)-6-(2,5,5-trimethylhexyloxymethyl)-4-methyl-phenol

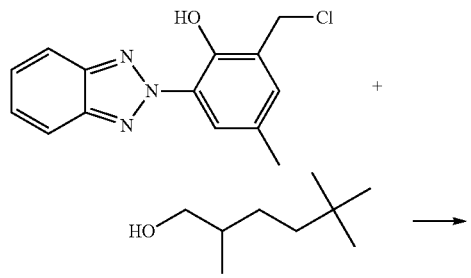

-continued

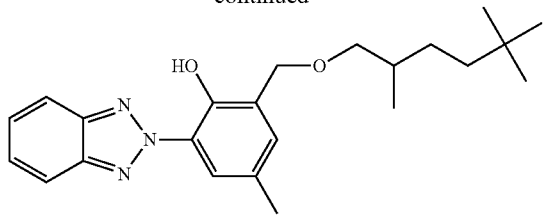

2-(2H-Benzotriazol-2-yl)-6-chloromethyl-4-methyl-phenol (7.0 g, 25.6 mmol) is partly solved in dioxane (190 mL) at 80° C. 2,5,5-Trimethyl-hexan-1-ol (124.1 g, 731 mmol) and sodium hydride (1.7 g, 42 mmol, 60% in mineral oil) are added subsequently. The orange reaction mixture is stirred at 80° C. for one hour and evaporated to dryness. The residue is dissolved in ethyl acetate and extracted with water. The organic layer is dried over sodium sulphate, filtered and evaporated to dryness. The crude product is purified by column chromatography (ethyl acetate/heptane 1:12) to yield 4.8 g of 2-(2H-Benzotriazol-2-yl)-6-(2,5,5-trimethylhexyloxymethyl)-4-methyl-phenol.

EXAMPLE 6

2-(2H-Benzotriazol-2-yl)-6-(3-methyl-butoxymethyl)-4-methyl-phenol

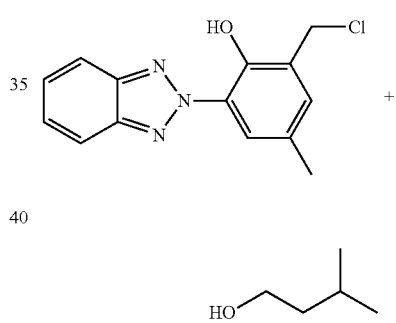

2-(2H-Benzotriazol-2-yl)-6-chloromethyl-4-methyl-phenol (10.0 g, 33 mmol) is suspended in a mixture of isoamyl alcohol (35 g, 0.4 mol) and acetone (5 g) and stirred at 80° C. for 30 minutes. Sodium carbonate (4.7 g, 44 mmol) is added and the reaction mixture is stirred at 80° C. for 30 minutes. Acetone is removed under vacuum, salts are filtered off and the reaction mixture is evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/ heptane 1:12) to yield 7.0 g of 2-(2H-Benzotriazol-2-yl)-6-(3-methyl-butoxymethyl)-4-methyl-phenol.

EXAMPLE 7

2-(2H-Benzotriazol-2-yl)-6-hexyloxymethyl-4-methyl-phenol

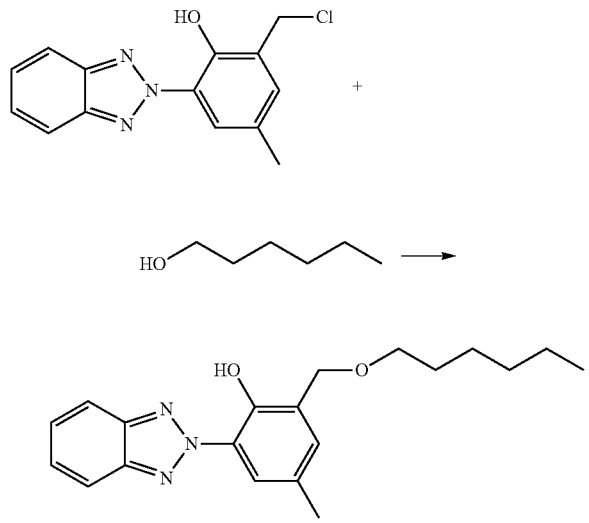

2-(2H-Benzotriazol-2-yl)-6-chloromethyl-4-methyl-phenol (1.0 g, 3.2 mmol) is partly solved in dioxane (19 g) at 80° C. and 1-hexanol (6.6 g, 65 mmol) and sodium hydride (0.2 g, 4.3 mmol, 60% in mineral oil) are added subsequently. The orange reaction mixture is stirred at 80° C. for 2 hours and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:30) to yield 940 mg of 2-(2H-Benzotriazol-2-yl)-6-hexyloxymethyl-4-methyl-phenol.

EXAMPLE 8

2-Ethyl-hexanoic acid 3-(2H-benzotriazol-2-yl)-2-hydroxy-5-methyl-benzyl ester

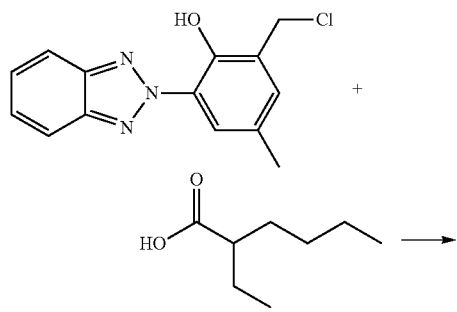

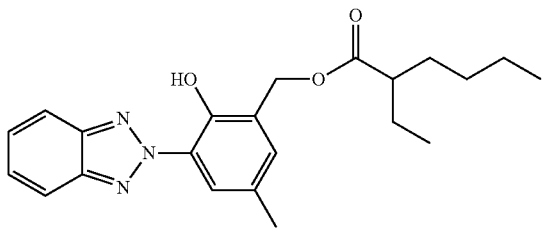

2-(2H-Benzotriazol-2-yl)-6-chloromethyl-4-methyl-phenol (10.0 g, 33 mmol) is suspended in a mixture of 2-ethylhexanoic acid (11.9 g, 82 mmol) and tetrahydrofuran (75 g) and stirred at 70° C. for 30 minutes. Sodium carbonate (10.5 g, 99 mmol) is added. The slightly yellow reaction mixture is stirred at 60° C. for 15 minutes and evaporated to dryness. The residue is dissolved in ethyl acetate and extracted with an aqueous potassium carbonate solution (10%) and brine. The organic layer is dried over sodium sulphate, filtered and evaporated to dryness. The crude product is purified by column chromatography (ethyl acetate/heptane 1:12) to yield 11.2 g of 2-Ethyl-hexanoic acid 3-(2H-benzotriazol-2-yl)-2-hydroxy-5-methyl-benzyl ester.

EXAMPLE 9

3-Methyl-butyric acid 3-(2H-benzotriazol-2-yl)-2-hydroxy-5-methyl-benzyl ester

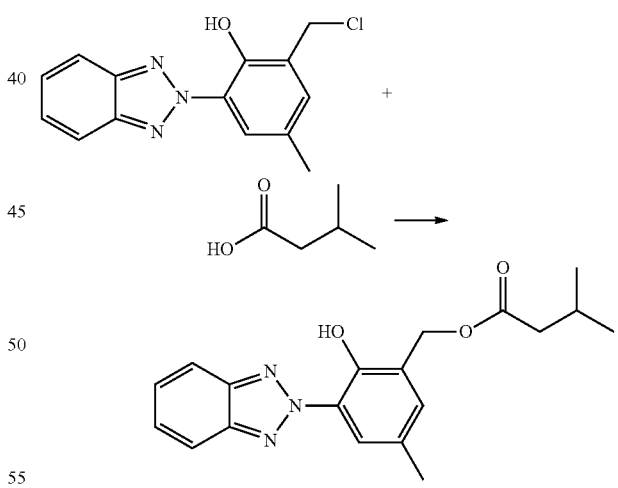

2-(2H-Benzotriazol-2-yl)-6-chloromethyl-4-methyl-phenol (10.0 g, 33 mmol) is suspended in a mixture of 2-isovaleric acid (8.4 g, 82 mmol) and tetrahydrofuran (75 g) and stirred at 70° C. for 30 minutes. Sodium carbonate (10.5 g, 99 mmol) is added. The reaction mixture is stirred at 60° C. for 15 minutes and evaporated to dryness. The residue is dissolved in ethyl acetate and extracted with an aqueous potassium carbonate solution (10%) and brine. The organic layer is dried over sodium sulphate, filtered and evaporated to dryness. The crude product is purified by column chromatography (ethyl acetate/heptane 1:12) to yield 11.5 g of 3-Methyl-butyric acid 3-(2H-benzotriazol-2-yl)-2-hydroxy-5-methyl-benzyl ester.

EXAMPLE 10

2-(5-Chloro-2H-benzotriazol-2-yl)-4-methyl-phenol

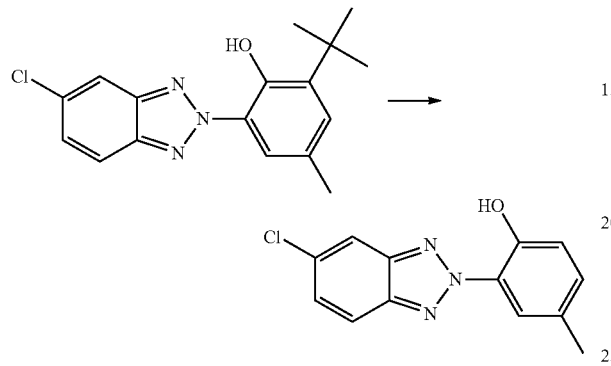

To a solution of 2-tert-Butyl-6-(5-chloro-2H-benzotriazol-2-yl)-4-methyl-phenol (50.0 g, 158 mmol) in toluene (700 ml) aluminium trichloride (42.2 g, 317 mmol) is added at 80° C. and the reaction mixture is stirred for 30 minutes, cooled to room temperature and slowly poured on crushed ice. The aqueous phase is extracted with ethyl acetate. The organic layer is washed with water, dried over sodium sulphate, filtered and evaporated to dryness. The crude product is purified by column chromatography (ethyl acetate/heptane 1:12) to yield 34.9 g of 2-(5-Chloro-2H-benzotriazol-2-yl)-4-methyl-phenol.

EXAMPLE 11

2-(5-Chloro-2H-benzotriazol-2-yl)-6-chloromethyl-4-methyl-phenol

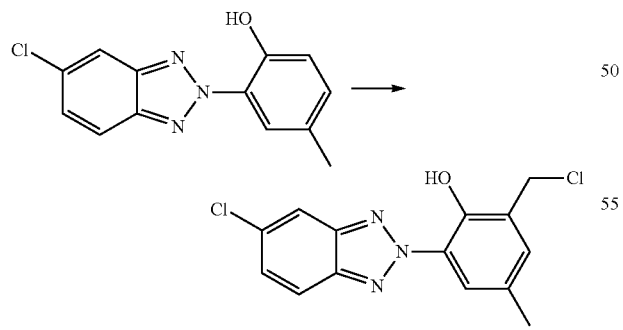

2-(5-Chloro-2H-benzotriazol-2-yl)-4-methyl-phenol (20.0 g, 77 mmol) is dissolved in acetic acid (90 mL) at 90° C. Zinc chloride (1.0 g, 7.7 mmol) and paraformaldehyde (9.2 g, 308 mmol) are added and HCl gas is passed through the reaction mixture for 12 hours at 90° C. The product, which precipitates after cooling to room temperature, is filtered off, washed with cold pentane and dried at 60° C. under vacuum to yield 21.4 g of 2-(5-Chloro-2H-benzotriazol-2-yl)-6-chloromethyl-4-methyl-phenol.

EXAMPLE 12

2-(5-Chloro-benzotriazol-2-yl)-6-(2-ethylhexyloxymethyl)-4-methyl-phenol

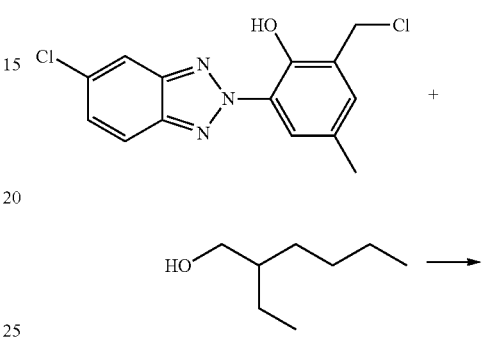

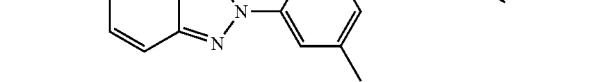

2-(5-Chloro-2H-benzotriazol-2-yl)-6-chloromethyl-4-methyl-phenol (5.0 g, 16 mmol) is suspended in a mixture of 2-ethylhexanol (20.0 g, 154 mmol) and acetone (5 g) and stirred at 80° C. for 15 minutes. Sodium carbonate (3.4 g, 32 mmol) is added. The slightly yellow reaction mixture is stirred at 80° C. for 3 hours and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 4.9 g of 2-(5-Chloro-benzotriazol-2-yl)-6-(2-ethylhexyloxymethyl)-4-methyl-phenol.

EXAMPLE 13

2-(5-Chloro-2H-benzotriazol-2-yl)-4-methyl-6-(3-methyl-butoxymethyl)-phenol

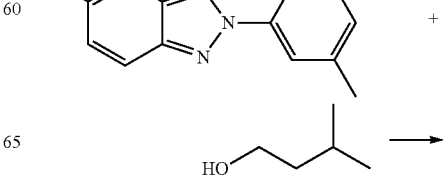

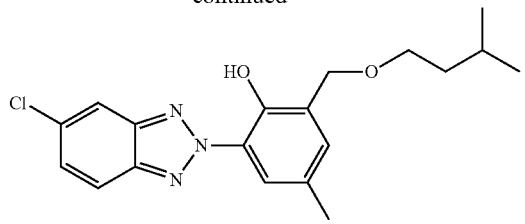

2-(5-Chloro-2H-benzotriazol-2-yl)-6-chloromethyl-4-methyl-phenol (5.0 g, 16 mmol) is suspended in a mixture of isoamyl alcohol (20.0 g, 227 mmol) and acetone (5 g) and stirred at 80° C. for 15 minutes. Sodium carbonate (2.1 g, 20 mmol) is added. The slightly yellow reaction mixture is stirred at 80° C. for 2 hours and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 4.7 g of 2-(5-Chloro-2H-benzotriazol-2-yl)-4-methyl-6-(3-methyl-butoxymethyl)-phenol.

EXAMPLE 14

Synthesis of 2-(2H-Benzotriazol-2-yl)-6-hydroxymethyl-4-methyl-phenol

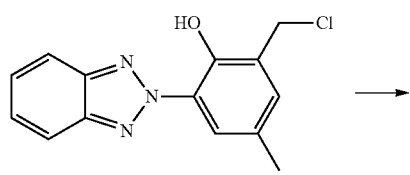

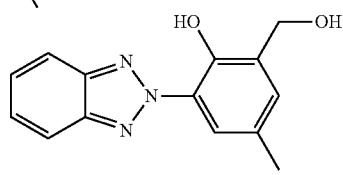

To a suspension of 2-(2H-Benzotriazol-2-yl)-6-chloromethyl-4-methyl-phenol (20.0 g, 73 mmol) in a mixture of tetrahydrofuran and water (180 g, 5:1) sodium bicarbonate (9.2 g, 110 mmol) is added. The reaction mixture is stirred at room temperature for 5 hours and evaporated to dryness. The crude product is purified by column chromatography (ethyl acetate/heptane 1:4) to yield 9.6 g of 2-(2H-Benzotriazol-2-yl)-6-hydroxymethyl-4-methyl-phenol.

EXAMPLE 15

3,3'-Bis(2H-benzotriazol-2-yl)-2,2'-dihydroxy-5,5'-dimethylbenzyl ether

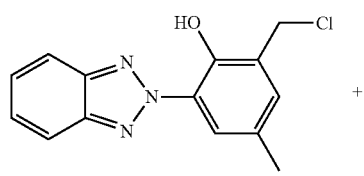

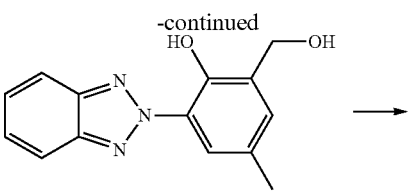

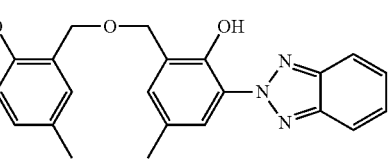

To a suspension of 2-(2H-Benzotriazol-2-yl)-6-chloromethyl-4-methyl-phenol (1.1 g, 3.9 mmol) and 2-(2H-benzotriazol-2-yl)-6-hydroxymethyl-4-methyl-phenol (1.1 g, 3.9 mmol) in toluene (50 mL) sodium carbonate (456 mg, 4.3 mmol) is added. The reaction mixture is stirred at 100° C. for 4 hours. The precipitated product is filtered off, washed with water and tetrahydrofuran, and dried at 70° C. under vacuum to yield 1.3 g of 3,3'-Bis(2H-benzotriazol-2-yl)-2,2'-dihydroxy-5,5'-dimethylbenzyl ether.

EXAMPLE 16

2-(2H-Benzotriazol-2-yl)-6-chloromethyl-4-(1,1,3,3-tetramethyl-butyl)-phenol

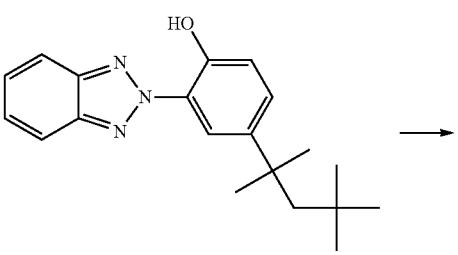

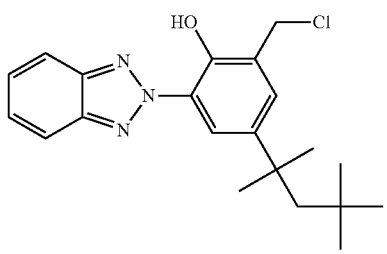

2-(2H-Benzotriazol-2-yl)-4-(1,1,3,3-tetramethyl-butyl) phenol (45.0 g, 140 mmol) is dissolved in acetic acid (200 mL) at 90° C. Zinc chloride (2.0 g, 14 mmol) and paraformaldehyde (18 g, 600 mmol) are added and HCl gas is passed through the reaction mixture for 12 hours at 90° C. The product, which precipitates after cooling to room temperature, is filtered off, washed with cold pentane and dried at 60°

C. under vacuum to yield 36 g of 2-(2H-Benzotriazol-2-yl)-6-chloromethyl-4-(1,1,3,3-tetramethyl-butyl)-phenol.

EXAMPLE 17

2-(2H-Benzotriazol-2-yl)-6-(3-methyl-butoxymethyl)-4-(1,1,3,3-tetramethyl-butyl)-phenol

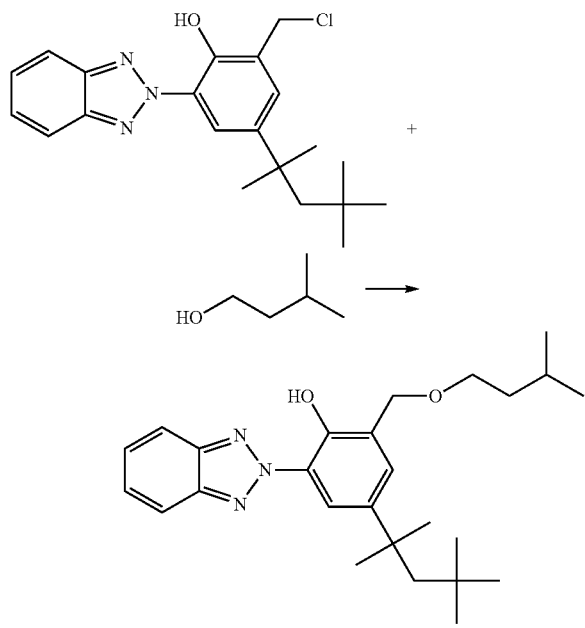

2-(2H-Benzotriazol-2-yl)-6-chloromethyl-4-(1,1,3,3-tetramethyl-butyl)-phenol (5.0 g, 13.5 mmol) is suspended in isoamyl alcohol (20.0 g, 227 mmol) and stirred at 80° C. for 15 minutes. Sodium hydride (0.2 g, 4.3 mmol, 60% in mineral oil) is added. The orange reaction mixture is stirred at 80° C. for 15 minutes and evaporated to dryness. The residue is dissolved in ethyl acetate and extracted with aqueous citric acid (5%) and brine. The organic layer is dried over sodium sulphate, filtered and evaporated to dryness. The crude product is purified by column chromatography (ethyl acetate/heptane 1:12) to yield 3.7 g of 2-(2H-Benzotriazol-2-yl)-6-(3-methyl-butoxymethyl)-4-(1,1,3,3-tetramethyl-butyl)-phenol.

EXAMPLE 18

Photostabilization of BMDBM 80 mg of BMDBM were dissolved in 720 mg $C_{12-15}$ alkyl benzoate. 1200 mg of ethanol were added. 2 mg/cm$^2$ of this solution were spread over six roughened glass plates. Three glass plates were stored in the dark while the three others were irradiated with 25 MED (ATLAS Suntester). Afterwards the oil film of each glass plate was separately dissolved in 30 mL methanol and the BMDBM content of these solutions quantified by HPLC. In comparison to unexposed films the average recovery of BMDBM after irradiation was determined to be 21%.

80 mg of BMDBM and 80 mg of 2-(2H-benzotriazol-2-yl)-6-(2-ethylhexyloxymethyl)-4-methyl-phenol were dissolved in 640 mg $C_{12-15}$ alkyl benzoate. 1200 mg of ethanol were added. 2 mg/cm$^2$ of this solution were spread over six roughened glass plates. Three glass plates were stored in the dark while the three others were irradiated with 25 MED (ATLAS Suntester). Afterwards the oil film of each glass plate was separately dissolved in 30 mL methanol and the BMDBM content of these solutions quantified by HPLC.

In comparison to unexposed films the average recovery of BMDBM after irradiation was determined to be 75%.

These results demonstrate that BMBDM can efficiently be stabilized by addition of 2-(2H-benzotriazol-2-yl)-6-(2-ethylhexyloxymethyl)-4-methyl-phenol.

EXAMPLE 19

Determination of the Solubility in Cosmetic Solvents 1.5 g of a cosmetic solvent (Capric/Caprylic Triglyceride (Mygliol 318) and $C_{12-15}$ Alkylbenzoate (Finsolv TN)) is saturated with the respective Benzotriazol-derivative by adding 0.2 g portions while stirring at room temperature. The saturated solution is stirred for 7 days at room temperature. 1 ml of the supernatant is centrifuged and filtered in order to obtain a clear solution. The concentration of the Benzotriazol-derivative is determined by means of HPLC.

TABLE 2

| Compound of example | Benzotriazole of formula (Ia) wherein | | Derivative | solubility | |
|---|---|---|---|---|---|
| | $R^3$ | $R^5$ | | Myritol 318 | Finsolv TN |
| 2 | H | —CH$_2$CH(C$_2$H$_5$)C$_4$H$_9$ (2-Ethylhexyl) | Ether | 66% | 64% |
| 8 | H | —COCH$_2$CH(C$_2$H$_5$)C$_4$H$_9$ (2-Ethylhexylcarbonyl) | Ester | 24% | 42% |
| 6 | H | —C$_2$H$_4$CH(CH$_3$)$_2$ (Isoamyl) | Ether | 36% | 37% |
| 9 | H | —COC$_2$H$_4$CH(CH$_3$)$_2$ (Isoamylcarbonyl) | Ester | 6% | 8% |
| 12 | Cl | —C$_2$H$_4$CH(CH$_3$)$_2$ (Isoamyl) | Ether | 12% | 19% |
| 14 | H | 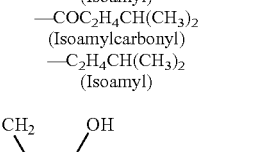 | Bis-Ether | 0.01% | 0.02% |

As can be retrieved from table 2 the alkyl-ether derivatives show a significantly higher solubility compared to the corresponding ester derivatives or the bis-ether of example 14.

EXAMPLE 20

Solubility of BMDBM in Various Mixtures of 2-(2H-Benzotriazol-2-yl)-6-(2-ethylhexyloxymethyl)-4-methyl-phenol (1A) and different cosmetic oils 20 mL of the corresponding cosmetic oil (see table 3) are saturated with BMDBM by adding 0.5 g (2.5%) portions while stirring at room temperature. The saturated solution is stirred for 7 days at room temperature. 1 mL of the supernatant is centrifuged and filtered in order to obtain a clear solution. The concentration of BMDBM is determined by means of HPLC.

The benzotriazole 1A is mixed with the corresponding solvent [w/w] as outlined in table 3 below resulting in clear solutions. 5 mL of the respective mixture are saturated with BMDBM by adding 125 mg (2.5%) portions while stirring at room temperature. The saturated solution is stirred for 7 days at room temperature. Afterwards 1 mL of the supernatant is centrifuged and filtered in order to obtain a clear solution. The concentration of BMDBM is determined by means of HPLC according to standard methods.

TABLE 3

| Solvent | Solubility BMDBM [w %] |
|---|---|
| caprylic/capric triglyceride | 13.3 |
| Mixture caprylic/capric triglyceride & benzotriazole 1A: 1:2 | 14.0 |
| diisopropyl sebacate | 18.8 |
| Mixture diisopropyl sebacate & benzotriazole 1A: 1:1 | 18.8 |
| dicaprylyl carbonate | 13.5 |
| Mixture dicaprylyl carbonate & benzotriazole 1A: 1:1 | 14.4 |
| $C_{12-14}$ alkyl benzoate | 15.3 |
| Mixture of $C_{12-14}$ alkyl benzoate & benzotriazole 1A: 1:1 | 15.3 |

As can be seen from the above presented results in table 3 the benzotriazole 1A can be used as solubilizer (i.e. replacer of the respective oil) in order to reduce the total amount of cosmetic solvent needed for the dissolution of BMDBM.

The invention claimed is:
1. Benzotriazole of formula (Ia):

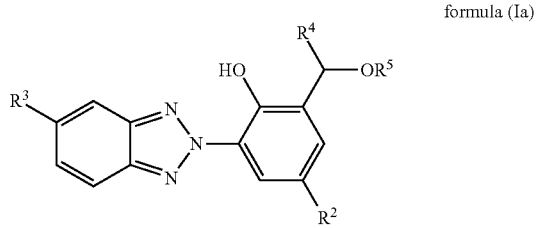

formula (Ia)

wherein
$R^2$ is hydrogen; $C_{1-30}$alkyl; $C_{1-5}$alkoxy; $C_{1-5}$alkoxycarbonyl; $C_{5-7}$cycloalkyl; $C_{6-10}$aryl or aralkyl;
$R^3$ is hydrogen; $C_{1-5}$alkyl; $C_{1-5}$alkoxy or halogen, preferably hydrogen or Cl;
$R^4$ is hydrogen or $C_{1-5}$alkyl;
$R^5$ is $C_{1-30}$alkyl or $C_{5-10}$cycloalkyl.

2. The benzotriazole according to claim 1, wherein the benzotriazole has the formula (II):

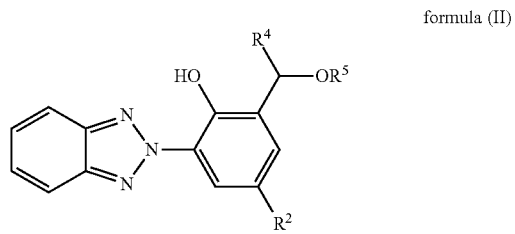

formula (II)

wherein
$R^2$ is hydrogen or $C_{1-12}$alkyl;
$R^4$ is hydrogen or $C_{1-2}$alkyl; and
$R^5$ is $C_{1-12}$alkyl or $C_{5-7}$cycloalkyl.

3. The benzotriazole according to claim 1, wherein $R^2$ is methyl; $R^4$ is hydrogen; and $R^5$ is $C_{5-10}$alkyl or $C_6$cycloalkyl.

4. The benzotriazole according to claim 1, wherein $R^2$ is methyl; $R^4$ is hydrogen; and $R^5$ is $C_{6-10}$alkyl or $C_6$cycloalkyl.

5. The benzotriazole according to claim 1, wherein $R^5$ is a branched alkyl or a methyl substituted cyclohexyl radical.

6. The benzotriazole according to claim 1, wherein $R^5$ is 2,5,5-trimethylhexyl, 3,5,5-trimethylhexyl, 3,3,5-trimethylcyclohexyl, isoamyl or 2-ethylhexyl.

7. A topical composition comprising a benzotriazole according to claim 1 and a cosmetically acceptable carrier.

8. A topical composition according to claim 7 further comprising butyl methoxydibenzoylmethane.

9. A topical composition according to claim 7 further comprising bis-ethylhexyloxyphenol methoxyphenyl triazine.

10. A topical composition according to claim 7 further comprising octocrylene.

11. A method for solubilizinq butyl methoxydibenzoylmethane comprising incorporating a benzotriazole according to claim 1 in a solubilizing effective amount into a composition comprising butyl methoxydibenzoylmethane and a cosmetic oil.

12. The method according to claim 11, wherein the cosmetic oil is $C_{12-15}$ alkyl benzoate, caprylic/capric triglyceride, dicaprylyl carbonate or diisopropyl sebacate.

13. A method of enhancing photostability of butyl methoxydibenzoylmethane comprising incorporating a benzotriazole according to claim 1 in a photostabilizing effective amount into a composition comprising butyl methoxydibenzoylmethane.

14. A process for the preparation of benzotriazoles according to claim 1 comprising the steps of:
(a.) chloroalkylation of a benzotriazole of formula (IIIa)

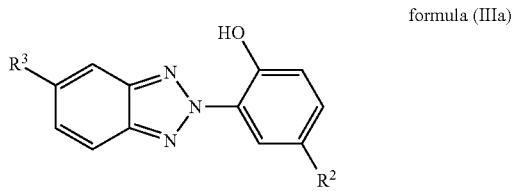

formula (IIIa)

with an aldehyde $R^4$CHO to thereby form a chloroalkylated benzotriazole thereof, followed by
(b.) ether formation by converting the chloroalkylated benzotriazole with an alcohol $R^5$OH in the presence of a base.

15. The process according to claim 14, wherein the aldehyde R$^4$CHO is selected from the group consisting of paraformaldehyde and acetaldehyde.

16. The process according to claim 14, wherein the alcohol R$^5$OH is at least one selected from the group consisting of isoamylalcohol, 2,5,5-trimethylhexan-1-ol, 2-ethylhexanol, 3,3,5-trimethyl-cyclohexanol, and 3,5,5-trimethylhexan-1ol.

\* \* \* \* \*